US010405968B2

(12) United States Patent  
Gustafson et al.

(10) Patent No.: US 10,405,968 B2  
(45) Date of Patent: Sep. 10, 2019

(54) IMPLANT HAVING FILAMENT LIMBS OF AN ADJUSTABLE LOOP DISPOSED IN A SHUTTLE SUTURE

(71) Applicant: Medos International Sàrl, Le Locle (CH)

(72) Inventors: Adam C. Gustafson, Dighton, MA (US); Meghan A. Pasquali, Providence, RI (US); David B. Spenciner, North Attleboro, MA (US); Mehmet Ziya Sengun, Canton, MA (US); Stephen J. Orphanos, Bridgewater, MA (US)

(73) Assignee: Medos International Sarl, Le Locle (CH)

( * ) Notice: Subject to any disclaimer, the term of this patent is extended or adjusted under 35 U.S.C. 154(b) by 1490 days.

(21) Appl. No.: 14/103,167

(22) Filed: Dec. 11, 2013

(65) Prior Publication Data

US 2015/0157449 A1  Jun. 11, 2015

(51) Int. Cl.
*A61F 2/08* (2006.01)  
*A61B 17/04* (2006.01)  
*A61B 17/06* (2006.01)

(52) U.S. Cl.
CPC ........ *A61F 2/0811* (2013.01); *A61B 17/0401* (2013.01); *A61B 17/06166* (2013.01); (Continued)

(58) Field of Classification Search
CPC .... A61F 2/0811; A61F 2/0063; A61F 2/0805; A61F 2002/0068; A61F 2002/0823; (Continued)

(56) References Cited

U.S. PATENT DOCUMENTS 2,600,395 A  6/1952 Domoj et al.  
4,093,292 A  6/1978 Marcet et al.  
(Continued)

FOREIGN PATENT DOCUMENTS

EP  2 238 944 A2  10/2010  
FR  2743294 A1  7/1997  
(Continued)

OTHER PUBLICATIONS

Extended European Search Report for Application No. 14197234.9, dated May 15, 2015 (7 pages).

*Primary Examiner* — Eric J Rosen  
*Assistant Examiner* — Chima U Igboko

(57) ABSTRACT

A device having an implantable body associated with at least two filaments or sutures and configured for use in soft tissue reconstructions is provided. One exemplary embodiment includes an implantable body, an adjustable filament loop for holding ligament grafts that is coupled to the body, and a shuttle suture removably coupled to the implantable body and configured for shuttling the body through at least a portion of a bone tunnel. The loop can be defined by a self-locking knot, and one or more loop-adjusting limbs can extend from the knot, with a portion of the limb(s) also extending into a hollow portion of the shuttle suture. In some embodiments having two adjustable limbs, an intermediate portion of each limb can be the portions disposed in respective hollow portions of the shuttle suture. Other configurations of devices and systems, as well as methods for performing ACL repairs, are also provided.

22 Claims, 13 Drawing Sheets

(52) U.S. Cl.
CPC ............. A61B 2017/0404 (2013.01); A61B 2017/0475 (2013.01); A61B 2017/06185 (2013.01); A61F 2002/0823 (2013.01); A61F 2002/0852 (2013.01); A61F 2002/0882 (2013.01)

(58) Field of Classification Search
CPC ...... A61F 2002/0817; A61F 2002/0835; A61F 2002/0841; A61F 2002/0847; A61F 2002/0858; A61F 2002/0864; A61F 2002/087; A61F 2002/0876; A61F 2002/0888; A61F 2002/0811; A61F 2002/0882; A61F 2002/0852; A61F 2002/0829; A61B 2017/0403; A61B 2017/0406; A61B 2017/0408; A61B 2017/0409; A61B 2017/0411; A61B 2017/0417; A61B 2017/0414; A61B 2017/0419; A61B 2017/0448; A61B 2017/0446; A61B 2017/0459; A61B 2017/0458; A61B 2017/0404; A61B 2017/0475; A61B 2017/0477; A61B 2017/06185; A61B 17/0401; A61B 17/12009; B65H 69/04
USPC .............................................. 289/1.2, 1.5, 13
See application file for complete search history.

(56) References Cited

U.S. PATENT DOCUMENTS

| | | | |
|---|---|---|---|
| 4,105,349 A | 8/1978 | Kupperman et al. |
| 4,133,604 A | 1/1979 | Fuller |
| 4,186,921 A | 2/1980 | Fox |
| 4,233,917 A | 11/1980 | Carnaby |
| 4,255,836 A | 3/1981 | Dunahoo |
| 4,257,309 A | 3/1981 | Dunahoo |
| 4,319,428 A | 3/1982 | Fox |
| 4,469,101 A | 9/1984 | Coleman et al. |
| 4,510,934 A | 4/1985 | Batra |
| 4,526,125 A | 7/1985 | Bain, Jr. |
| 4,527,564 A | 7/1985 | Eguchi et al. |
| 4,582,165 A | 4/1986 | Latini |
| 4,604,821 A | 8/1986 | Moser |
| 4,705,040 A | 11/1987 | Mueller et al. |
| 4,723,634 A | 2/1988 | Fisk |
| 4,750,492 A | 6/1988 | Jacobs |
| 4,773,910 A | 9/1988 | Chen et al. |
| 4,781,191 A | 11/1988 | Thompson |
| 4,854,138 A | 8/1989 | Charland |
| 4,890,363 A | 1/1990 | Cross |
| 4,910,834 A | 3/1990 | Minkler |
| 4,946,377 A | 8/1990 | Kovach |
| 4,962,929 A | 10/1990 | Melton, Jr. |
| 4,971,075 A | 11/1990 | Lee |
| 5,062,344 A | 11/1991 | Gerker |
| 5,074,291 A | 12/1991 | Carter |
| 5,083,875 A | 1/1992 | Cedrone |
| 5,139,520 A | 8/1992 | Rosenberg |
| 5,149,329 A | 9/1992 | Richardson |
| 5,150,766 A | 9/1992 | Bell |
| 5,168,605 A | 12/1992 | Bartlett |
| 5,178,629 A | 1/1993 | Kammerer |
| 5,219,359 A | 6/1993 | McQuilkin et al. |
| 5,269,783 A | 12/1993 | Sander |
| 5,306,290 A | 4/1994 | Martins et al. |
| 5,306,301 A | 4/1994 | Graf et al. |
| 5,374,268 A | 12/1994 | Sander |
| 5,374,269 A | 12/1994 | Rosenberg |
| 5,451,203 A | 9/1995 | Lamb |
| 5,505,735 A | 4/1996 | Li |
| 5,531,759 A | 7/1996 | Kensey et al. |
| 5,540,703 A | 7/1996 | Barker, Jr. et al. |
| 5,573,286 A | 11/1996 | Rogozinski |
| 5,575,819 A | 11/1996 | Amis |
| 5,628,756 A | 5/1997 | Barker |
| 5,649,541 A | 7/1997 | Stuckey |
| 5,667,528 A | 9/1997 | Colligan |
| 5,693,060 A | 12/1997 | Martin |
| 5,707,373 A | 1/1998 | Sevrain et al. |
| 5,769,894 A | 6/1998 | Ferragamo |
| 5,778,904 A | 7/1998 | Elsner |
| 5,921,986 A | 7/1999 | Bonutti |
| 5,928,267 A | 7/1999 | Bonutti et al. |
| 5,984,926 A | 11/1999 | Jones |
| 5,989,252 A | 11/1999 | Fumex |
| 6,009,882 A | 1/2000 | Schine et al. |
| 6,030,007 A | 2/2000 | Bassily et al. |
| 6,045,551 A | 4/2000 | Bonutti |
| 6,056,752 A | 5/2000 | Roger |
| 6,076,532 A | 6/2000 | Thomas et al. |
| 6,117,160 A | 9/2000 | Bonutti |
| 6,143,029 A | 11/2000 | Rippstein |
| 6,203,572 B1 | 3/2001 | Johnson et al. |
| 6,238,395 B1 | 5/2001 | Bonutti |
| 6,258,091 B1 | 7/2001 | Sevrain et al. |
| 6,293,961 B2 | 9/2001 | Schwartz et al. |
| 6,296,659 B1 | 10/2001 | Foerster |
| 6,306,159 B1 | 10/2001 | Schwartz |
| 6,319,271 B1 | 11/2001 | Schwartz |
| 6,342,060 B1 | 1/2002 | Adams |
| 6,418,576 B1 | 7/2002 | Starkweather |
| 6,453,974 B1 | 9/2002 | Lai et al. |
| 6,503,267 B2 | 1/2003 | Bonutti et al. |
| 6,517,578 B2 | 2/2003 | Hein |
| 6,527,795 B1 | 3/2003 | Lizardi |
| 6,533,802 B2 | 3/2003 | Bojarski et al. |
| 6,558,389 B2 | 5/2003 | Clark et al. |
| 6,589,244 B1 | 7/2003 | Sevrain et al. |
| 6,592,609 B1 | 7/2003 | Bonutti |
| 6,599,319 B2 | 7/2003 | Knudsen et al. |
| 6,602,290 B2 | 8/2003 | Esnouf et al. |
| 6,638,279 B2 | 10/2003 | Bonutti |
| 6,972,027 B2 | 12/2005 | Fallin et al. |
| 6,997,480 B2 | 2/2006 | Legrand |
| 6,997,940 B2 | 2/2006 | Bonutti |
| 7,033,380 B2 | 4/2006 | Schwartz et al. |
| 7,076,845 B2 | 7/2006 | Tylaska et al. |
| 7,150,757 B2 | 12/2006 | Fallin et al. |
| 7,235,091 B2 | 6/2007 | Thornes |
| 7,285,124 B2 | 10/2007 | Foerster |
| 7,306,417 B2 | 12/2007 | Dorstewitz |
| 7,390,332 B2 | 6/2008 | Selvitelli et al. |
| 7,407,512 B2 | 8/2008 | Bojarski et al. |
| 7,442,210 B2 | 10/2008 | Segal et al. |
| 7,481,825 B2 | 1/2009 | Bonutti |
| 7,500,990 B2 | 3/2009 | Whelan |
| 7,566,339 B2 | 7/2009 | Fallin et al. |
| 7,594,923 B2 | 9/2009 | Fallin et al. |
| 7,601,165 B2 | 10/2009 | Stone |
| 7,628,795 B2 | 12/2009 | Karwoski et al. |
| 7,641,694 B1 | 1/2010 | Goble et al. |
| 7,654,321 B2 | 2/2010 | Zazovsky et al. |
| 7,658,751 B2 | 2/2010 | Stone et al. |
| 7,682,374 B2 | 3/2010 | Foerster et al. |
| 7,686,838 B2 | 3/2010 | Wolf et al. |
| 7,703,372 B1 | 4/2010 | Shakespeare |
| 7,722,644 B2 | 5/2010 | Fallin et al. |
| 7,749,250 B2 | 7/2010 | Stone et al. |
| 7,776,039 B2 | 8/2010 | Bernstein et al. |
| 7,806,909 B2 | 10/2010 | Fallin et al. |
| 7,845,669 B2 | 12/2010 | Yeh et al. |
| 7,846,181 B2 | 12/2010 | Schwartz et al. |
| 7,857,830 B2 | 12/2010 | Stone et al. |
| 7,875,057 B2 | 1/2011 | Cook et al. |
| 7,875,058 B2 | 1/2011 | Holmes, Jr. |
| 7,887,551 B2 | 2/2011 | Bojarski et al. |
| 7,892,238 B2 | 2/2011 | DiPoto et al. |
| 7,892,256 B2 | 2/2011 | Grafton et al. |
| 7,901,431 B2 | 3/2011 | Shurnas |
| 7,905,903 B2 | 3/2011 | Stone et al. |
| 7,959,650 B2 | 6/2011 | Kaiser et al. |
| 8,012,171 B2 | 9/2011 | Schmieding |

(56) References Cited

U.S. PATENT DOCUMENTS

| | | | |
|---|---|---|---|
| 8,088,130 B2 | 1/2012 | Kaiser et al. | |
| 8,118,836 B2 | 2/2012 | Denham et al. | |
| 8,127,652 B1 | 3/2012 | Hennings et al. | |
| 8,128,658 B2 | 3/2012 | Kaiser et al. | |
| 8,136,438 B2 | 3/2012 | Shakespeare | |
| 8,137,382 B2 | 3/2012 | Denham et al. | |
| 8,147,514 B2 | 4/2012 | Bonutti | |
| 8,202,298 B2 | 6/2012 | Cook et al. | |
| 8,221,455 B2 | 7/2012 | Shurnas et al. | |
| 8,231,654 B2 | 7/2012 | Kaiser et al. | |
| 8,257,394 B2 | 9/2012 | Saadat et al. | |
| 8,298,271 B2 | 10/2012 | Jacene et al. | |
| 8,366,744 B2 | 2/2013 | Bojarski et al. | |
| 8,388,655 B2 | 3/2013 | Fallin et al. | |
| 8,398,678 B2 | 3/2013 | Baker et al. | |
| 8,439,976 B2 | 5/2013 | Albertorio et al. | |
| 8,460,379 B2 | 6/2013 | Albertorio et al. | |
| 8,475,534 B2 | 7/2013 | Karnes et al. | |
| 8,512,376 B2 | 8/2013 | Thornes | |
| 8,523,943 B2 | 9/2013 | Hart | |
| 8,535,313 B1 | 9/2013 | Masson | |
| 8,591,578 B2 | 11/2013 | Albertorio et al. | |
| 8,617,185 B2 | 12/2013 | Bonutti et al. | |
| 8,628,573 B2 | 1/2014 | Roller et al. | |
| 8,753,375 B2 | 6/2014 | Albertorio | |
| 8,790,370 B2 | 7/2014 | Spenciner et al. | |
| 8,808,329 B2 | 8/2014 | Bonutti | |
| 8,864,797 B2 * | 10/2014 | Justin | A61B 17/0487 606/232 |
| 8,876,900 B2 | 11/2014 | Guederian et al. | |
| 8,882,816 B2 | 11/2014 | Kartalian et al. | |
| 8,888,815 B2 | 11/2014 | Holmes, Jr. | |
| 8,936,621 B2 * | 1/2015 | Denham | A61B 17/0401 606/232 |
| 8,961,575 B2 | 2/2015 | Choinski | |
| 8,998,904 B2 | 4/2015 | Zeetser et al. | |
| 9,005,245 B2 | 4/2015 | Thornes et al. | |
| 9,072,510 B2 | 7/2015 | Thornes et al. | |
| 2002/0029066 A1 | 3/2002 | Foerster | |
| 2003/0005557 A1 | 1/2003 | Renn | |
| 2004/0153153 A1 | 8/2004 | Elson et al. | |
| 2006/0064126 A1 | 3/2006 | Fallin et al. | |
| 2006/0089646 A1 | 4/2006 | Bonutti | |
| 2006/0190042 A1 | 8/2006 | Stone et al. | |
| 2008/0027446 A1 | 1/2008 | Stone et al. | |
| 2008/0046009 A1 | 2/2008 | Albertorio et al. | |
| 2008/0287991 A1 | 11/2008 | Fromm | |
| 2009/0082805 A1 | 3/2009 | Kaiser et al. | |
| 2009/0182335 A1 * | 7/2009 | Struhl | A61B 17/0401 606/60 |
| 2009/0234377 A1 | 9/2009 | Mahlin et al. | |
| 2009/0281568 A1 | 11/2009 | Cendan et al. | |
| 2009/0312776 A1 | 12/2009 | Kaiser et al. | |
| 2009/0312792 A1 | 12/2009 | Fallin et al. | |
| 2010/0069926 A1 | 3/2010 | Goble et al. | |
| 2010/0106194 A1 | 4/2010 | Bonutti et al. | |
| 2010/0249809 A1 | 9/2010 | Singhatat et al. | |
| 2010/0256677 A1 | 10/2010 | Albertorio et al. | |
| 2010/0268273 A1 | 10/2010 | Albertorio et al. | |
| 2010/0292733 A1 | 11/2010 | Hendricksen et al. | |
| 2010/0305585 A1 | 12/2010 | Fallin et al. | |
| 2010/0318126 A1 | 12/2010 | Fallin et al. | |
| 2011/0022061 A1 | 1/2011 | Orphanos et al. | |
| 2011/0022083 A1 | 1/2011 | DiMatteo et al. | |
| 2011/0060375 A1 | 3/2011 | Bonutti | |
| 2011/0077667 A1 | 3/2011 | Singhatat et al. | |
| 2011/0098727 A1 | 4/2011 | Kaiser et al. | |
| 2011/0144699 A1 | 6/2011 | Fallin et al. | |
| 2011/0152927 A1 | 6/2011 | Deng et al. | |
| 2011/0160749 A1 | 6/2011 | Gordon et al. | |
| 2011/0160856 A1 | 6/2011 | Sinnott et al. | |
| 2011/0190815 A1 | 8/2011 | Saliman | |
| 2011/0208240 A1 | 8/2011 | Stone et al. | |
| 2011/0218625 A1 | 9/2011 | Berelsman et al. | |
| 2011/0238111 A1 | 9/2011 | Frank | |
| 2011/0276137 A1 | 11/2011 | Seedhom et al. | |
| 2011/0301708 A1 | 12/2011 | Stone et al. | |
| 2012/0046693 A1 | 2/2012 | Denham et al. | |
| 2012/0046747 A1 | 2/2012 | Justin et al. | |
| 2012/0053630 A1 | 3/2012 | Denham et al. | |
| 2012/0059416 A1 * | 3/2012 | Justin | A61B 17/0401 606/232 |
| 2012/0059468 A1 | 3/2012 | Mattern et al. | |
| 2012/0065731 A1 | 3/2012 | Justin et al. | |
| 2012/0065732 A1 | 3/2012 | Roller et al. | |
| 2012/0109129 A1 | 5/2012 | Bernstein | |
| 2012/0109194 A1 | 5/2012 | Miller et al. | |
| 2012/0116452 A1 | 5/2012 | Stone et al. | |
| 2012/0123474 A1 | 5/2012 | Zajac et al. | |
| 2012/0123541 A1 | 5/2012 | Albertorio et al. | |
| 2012/0130424 A1 * | 5/2012 | Sengun | A61B 17/0401 606/232 |
| 2012/0150203 A1 | 6/2012 | Brady et al. | |
| 2012/0150297 A1 | 6/2012 | Denham et al. | |
| 2012/0158051 A1 | 6/2012 | Foerster | |
| 2012/0158053 A1 | 6/2012 | Paulos | |
| 2012/0165867 A1 | 6/2012 | Denham et al. | |
| 2012/0165938 A1 | 6/2012 | Denham et al. | |
| 2012/0290002 A1 | 11/2012 | Astorino | |
| 2012/0290004 A1 | 11/2012 | Lombardo et al. | |
| 2012/0290006 A1 | 11/2012 | Collins et al. | |
| 2012/0296375 A1 | 11/2012 | Thal | |
| 2012/0303051 A1 | 11/2012 | Saadat et al. | |
| 2012/0310279 A1 | 12/2012 | Sikora et al. | |
| 2013/0023942 A1 | 1/2013 | Wyman et al. | |
| 2013/0035722 A1 | 2/2013 | McDevitt et al. | |
| 2013/0066371 A1 | 3/2013 | Rogers et al. | |
| 2013/0096612 A1 | 4/2013 | Zajac et al. | |
| 2013/0123810 A1 | 5/2013 | Brown et al. | |
| 2013/0123841 A1 | 5/2013 | Lyon | |
| 2013/0138150 A1 | 5/2013 | Baker et al. | |
| 2013/0165972 A1 | 6/2013 | Sullivan | |
| 2013/0165973 A1 | 6/2013 | Fallin et al. | |
| 2013/0172944 A1 | 7/2013 | Fritzinger et al. | |
| 2013/0197576 A1 | 8/2013 | Catania et al. | |
| 2013/0197577 A1 | 8/2013 | Wolf et al. | |
| 2013/0197578 A1 | 8/2013 | Gregoire et al. | |
| 2013/0197579 A1 | 8/2013 | Foerster et al. | |
| 2013/0197580 A1 * | 8/2013 | Perriello | A61F 2/0811 606/232 |
| 2013/0268000 A1 | 10/2013 | Harner et al. | |
| 2013/0268073 A1 | 10/2013 | Albertorio et al. | |
| 2013/0296931 A1 * | 11/2013 | Sengun | A61B 17/0401 606/228 |
| 2013/0317544 A1 | 11/2013 | Ferguson et al. | |
| 2014/0074239 A1 | 3/2014 | Albertorio et al. | |
| 2014/0081399 A1 | 3/2014 | Roller et al. | |
| 2014/0142627 A1 | 5/2014 | Hendricksen et al. | |
| 2014/0257346 A1 | 9/2014 | Sengun et al. | |
| 2014/0330312 A1 | 11/2014 | Spenciner et al. | |
| 2015/0073477 A1 | 3/2015 | Holmes, Jr. | |

FOREIGN PATENT DOCUMENTS

| | | | |
|---|---|---|---|
| JP | 2001198147 A * | 7/2001 | A61F 2/08 |
| JP | 2013233434 A * | 11/2013 | A61B 17/0401 |
| WO | 92/006648 A1 | 4/1992 | |

* cited by examiner

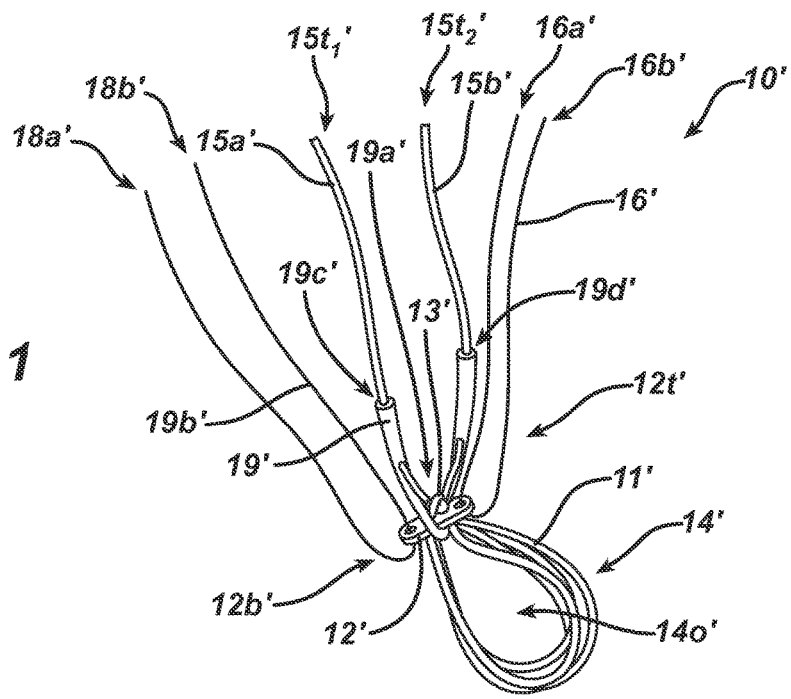
FIG. 1
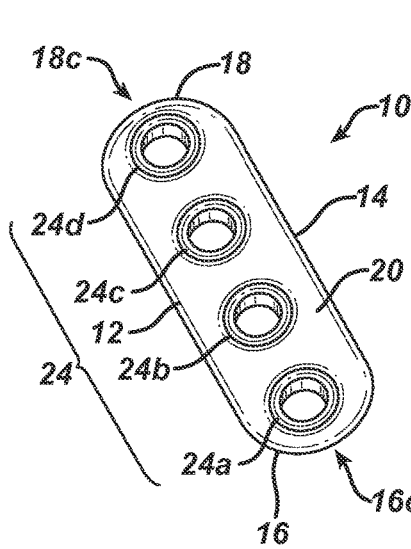
FIG. 2A
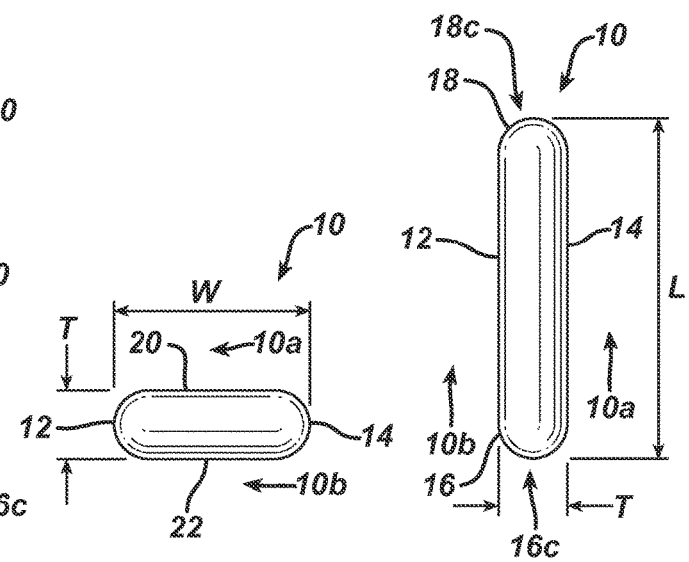
FIG. 2B
FIG. 2C

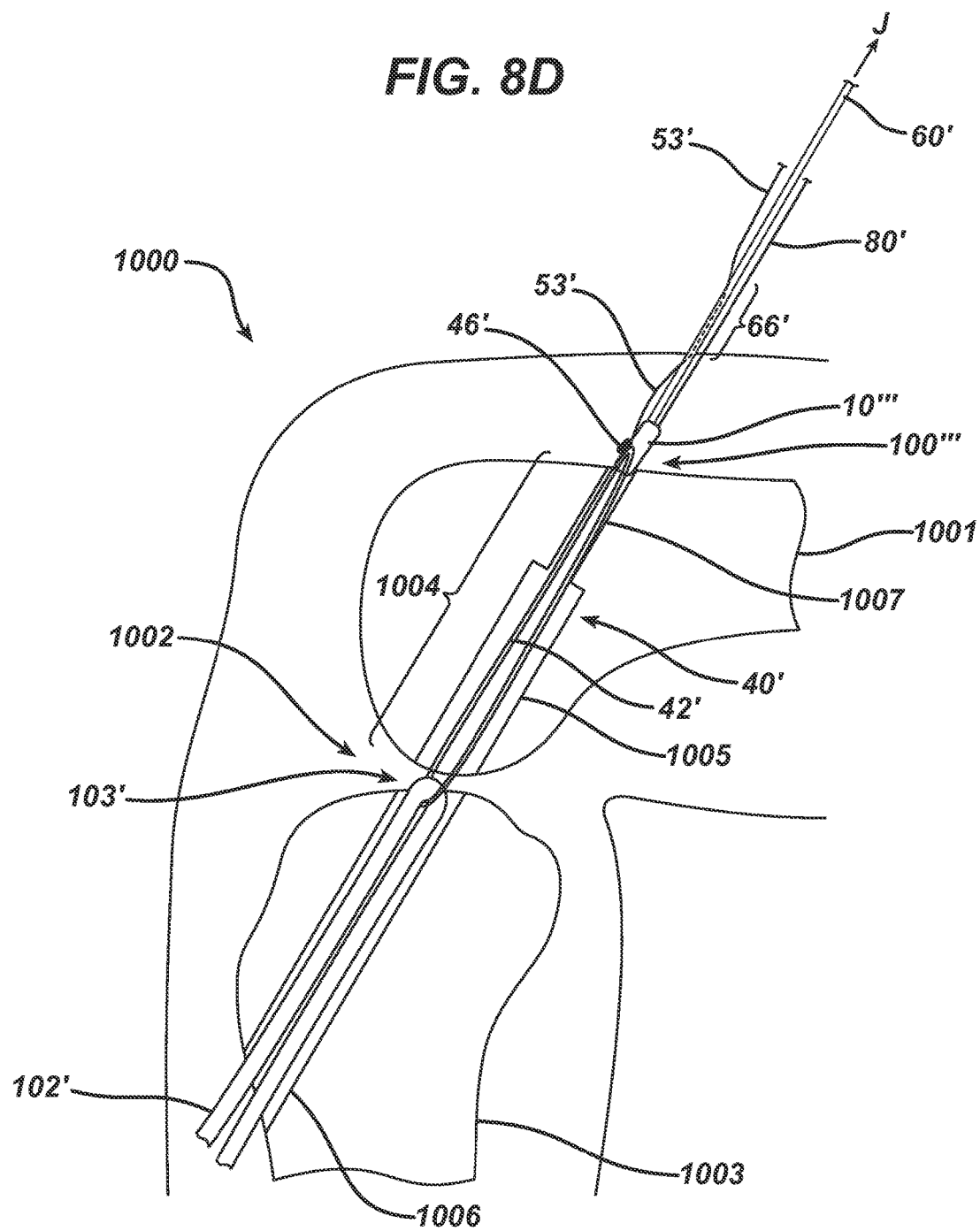

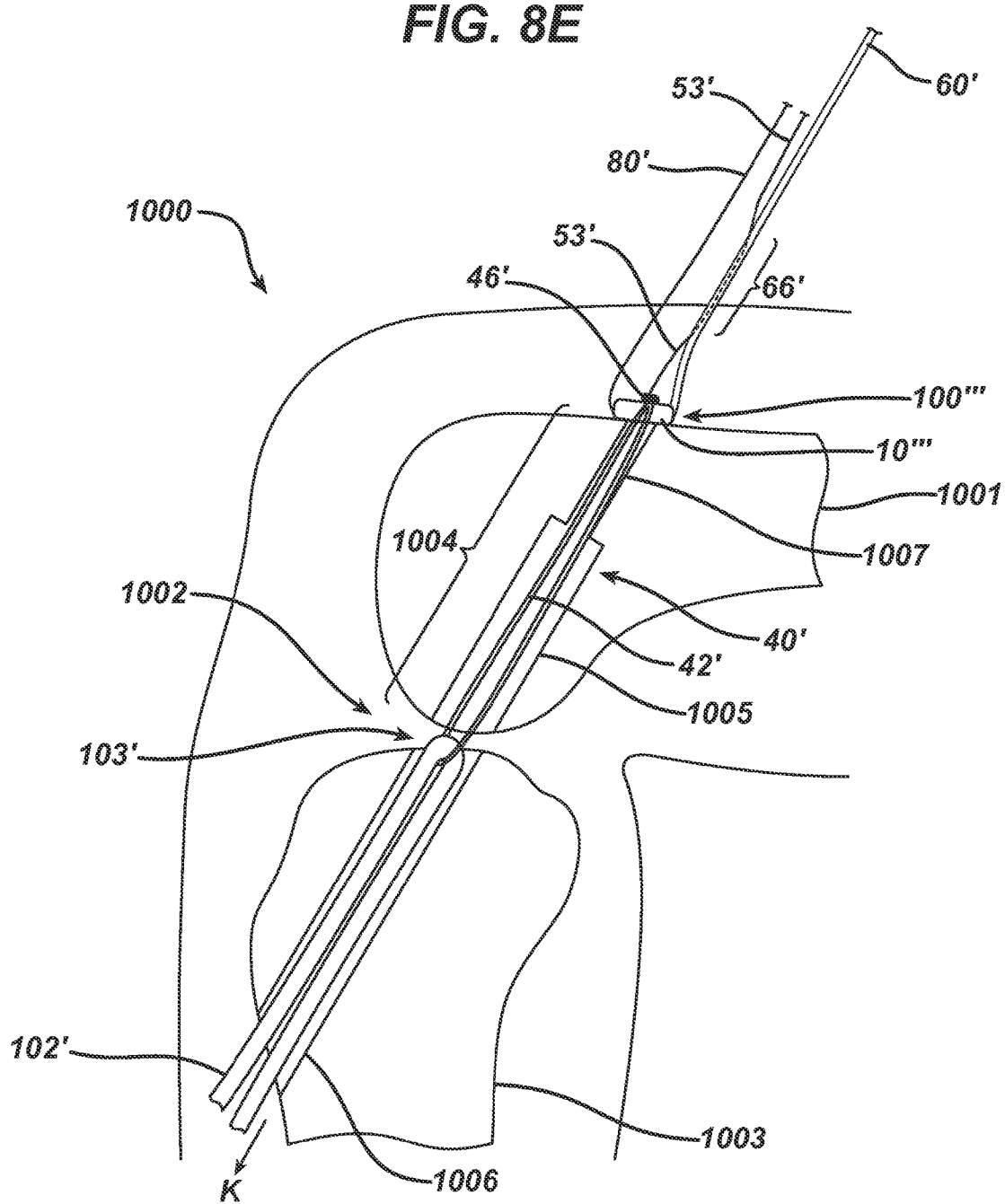

IMPLANT HAVING FILAMENT LIMBS OF AN ADJUSTABLE LOOP DISPOSED IN A SHUTTLE SUTURE

FIELD

The present disclosure relates to devices, systems, and methods for securing soft tissue to bone, and more particularly it relates to securing an ACL graft to a femur.

BACKGROUND

Joint injuries may commonly result in the complete or partial detachment of ligaments, tendons, and soft tissues from bone. Tissue detachment may occur in many ways, e.g., as the result of an accident such as a fall, overexertion during a work related activity, during the course of an athletic event, or in any one of many other situations and/or activities. These types of injuries are generally the result of excess stress or extraordinary forces being placed upon the tissues.

In the case of a partial detachment, commonly referred to under the general term "sprain," the injury frequently heals without medical intervention, the patient rests, and care is taken not to expose the injury to undue strenuous activities during the healing process. If, however, the ligament or tendon is completely detached from its attachment site on an associated bone or bones, or if it is severed as the result of a traumatic injury, surgical intervention may be necessary to restore full function to the injured joint. A number of conventional surgical procedures exist for re-attaching such tendons and ligaments to bone.

One such procedure involves forming aligned femoral and tibial tunnels in a knee to repair a damaged anterior cruciate ligament ("ACL"). In one ACL repair procedure, a ligament graft is associated with a surgical implant and secured to the femur. A common ACL femoral fixation means includes an elongate "button," sometimes referred to as a cortical button. The cortical button is attached to a suture loop that is sized to allow an adequate length of a soft tissue graft to lie within the femoral tunnel while providing secure extra-cortical fixation.

Existing devices and methods for surgical repairs have a number of limitations. For example, existing devices and methods do not always provide the desired strength. In some instances, one or more knots tied to help maintain a location of the suture loop with respect to a cortical button, and thus the graft associated therewith, can loosen or slip. Thus, even if a ligament graft is disposed at a desired location during a procedure, post-operatively the circumference of the loop can increase, causing the graft to move away from the desired location. The use of knots in conjunction with existing devices and methods can also be undesirable because of the additional surface area they provide, thereby increasing the risk of trauma at the surgical site.

Existing devices and methods also lack adjustability in many instances. For example, in procedures in which multiple ligament grafts are associated with the cortical button, it can be difficult to control placement of one ligament graft without also moving the other ligament graft. Still further, existing devices and methods often posses suture management issues. Many devices and methods use a plurality of sutures or filaments to guide and manipulate the button and associated ligament graft(s) to desired locations. The filaments can become tangled, difficult to identify during the course of a procedure, and cumbersome due to the total volume of filaments disposed in the bone tunnel. Additionally, although at least some of the filaments used to implant the button can be removed after implantation, it can be difficult to remove the filaments. As a result, in some instances, filaments can remain implanted in the body even though they serve no purpose after button implantation. Portions of filaments located at the surgical site can be cut after the button is delivered. To the extent filaments are cut, however, care should be taken to not cut too much of the filament. In some instances, a sleeve can be disposed around a portion of a filament extending from a knot to help indicate to a surgeon where to cut the filament. The sleeve, however, may bunch within the bone tunnel.

Accordingly, it is desirable to provide devices, systems, and methods that improve the strength and adjustability of surgical implants used in conjunction with ligament graft insertion, to minimize the number of knots associated with maintaining a location of the grafts once the grafts are disposed at desired locations, and to make it easy to remove filaments from a surgical site after implantation has occurred.

SUMMARY

Devices, systems, and methods are generally provided for performing soft tissue (e.g., ACL) repairs. In one exemplary embodiment, a surgical implant includes an implantable body, an adjustable filament loop coupled to the body, and a shuttle suture removably coupled to the implantable body. The adjustable filament loop can have at least one adjustable limb extending therefrom, and it can be configured to adjust a size of the loop when tension is applied to the limb. The shuttle suture can have at least a portion of it that is hollow, and the at least one adjustable limb can extend from the filament loop, into the hollow portion, and exit out of the shuttle suture at a location that is more remote from the implantable body than a location at which the adjustable limb enters the shuttle suture.

The implantable body can include a plurality of thru-holes formed in it. The adjustable filament loop can be disposed through at least two of the thru-holes, and the shuttle suture can be disposed through at least one of the thru-holes. In some embodiments the thru-hole through which the shuttle suture is disposed can be s different thru-hole than any thru-hole through which the adjustable filament loop is disposed. In some embodiments the adjustable loop can include a plurality of coils formed as a result of suture of the adjustable filament loop being disposed through at least two of the plurality of thru-holes of the body such that a portion of each coil is disposed on the top side of the body and a portion of each coil is disposed on a bottom side of the body.

The adjustable filament loop can include a self-locking knot formed on a top side of the body. In some embodiments the at least one adjustable limb includes a first adjustable limb and a second adjustable limb. The first adjustable limb can extend into a first hollow portion of the shuttle suture, and the second adjustable limb can extend into a second hollow portion of the shuttle suture. The at least one adjustable limb can enter the hollow portion of the shuttle suture at a location such that it is configured to form an acute angle with a longitudinal axis extending through a length of the implantable body.

The shuttle suture can be disposed through a thru-hole formed in the implantable body, and it can be configured to guide the implantable body, and the adjustable loop coupled thereto, through a passageway. In some embodiments the shuttle suture can be configured to bunch in the hollow portion of the shuttle suture when tension is applied to the at least one adjustable limb in a first direction, away from the implantable body, and a force is applied to the shuttle suture in a second, substantially opposite direction, toward the implantable body.

Another exemplary embodiment of a surgical implant includes a body having a plurality of thru-holes formed therein, a first suture filament extending through the body, and a second suture filament removably disposed through a thru-hole of the plurality of thru-holes. The first suture filament can be configured to form a self-locking knot and one or more coils. The self-locking knot can define a collapsible opening. The one or more coils can be arranged such that each coil is formed as a result of the first suture filament being disposed through at least two of the plurality of thru-holes of the body such that a portion of each coil is disposed on the top side of the body and a portion of each coil is disposed on a bottom side of the body. First and second terminal ends of the first suture filament can extend from the self-locking knot, and can be configured to adjust a size of one or more of the coils when tension is applied to one or both of the terminal ends. The second suture filament can have at least a portion of a first limb that is hollow, and at least a portion of a second limb that is hollow. The first terminal end of the first suture filament can be disposed in at least a portion of the hollow portion of the first limb, while the second terminal end of the first suture filament can be disposed in at least a portion the hollow portion of the second limb.

A location at which each of the first and second terminal ends of first suture filament exit the second suture filament can be more remote from the body of the implant than a location at which the terminal ends entered the second suture filament when tension is applied to the second suture filament. The first terminal end can enter a portion of the hollow portion of the first limb at a location such that it forms an acute angle with a longitudinal axis extending through a length of the body, and the second terminal end can enter a portion of the hollow portion of the second limb at a location such that it forms an acute angle with the longitudinal axis extending through the length of the body.

The second suture filament can be configured to bunch in the hollow portions when tension is applied to the first and second terminal ends in a first direction, away from the body, and a force is applied to the second suture filament in a second, substantially opposite direction, toward the body. In some embodiments a thru-hole through which the second suture filament is disposed can be a different thru-hole than the at least two thru-holes through which the first filament is disposed. In some embodiments the thru-hole through which the second suture filament is disposed can be an end thru-hole. A vertical distance between the top side of the body and a location at which the first one of the first and second terminal ends enters the second suture can be in the range of about 5 millimeters to about 50 millimeters. A length of at least one of the first and second terminal ends disposed in the hollow portion of the second filament can be in the range of about 10 millimeters to about 100 millimeters.

One exemplary embodiment of a surgical method includes loading a graft onto an adjustable filament loop that is coupled to an implant body. The adjustable filament loop can have at least one adjustable limb extending therefrom, and the implant body can have a shuttle filament disposed therethrough. Further, the adjustable limb can have a segment disposed in a hollow portion of the shuttle filament with a terminal end of the adjustable limb exiting the shuttle filament at a location that is more remote from an entry point of the segment into the shuttle filament. The method can further include pulling the shuttle filament, the implant body, the adjustable filament loop, and the graft, through a bone tunnel until the implant body exits the tunnel while at least a portion of the adjustable filament loop and the graft remain in the tunnel. Still further, the method can include orienting the implant body so that a bottom side of the implant body is facing the tunnel such that the adjustable filament loop is disposed substantially within the tunnel and the at least one adjustable limb is outside of the tunnel, adjacent to a top side of the implant body.

In some embodiments the method can further include applying tension to the at least one adjustable limb in a first direction, away from the implant body, and cutting the shuttle filament and the at least one adjustable limb so that the shuttle filament and the excess limb can be removed. The shuttle filament and the at least one adjustable limb can be cut at a variety of locations, but in some embodiments they can be cut at a location that is approximately between a location at which the terminal end of the adjustable limb enters the shuttle filament and a location at which the terminal end of the adjustable limb exits the shuttle filament. In some other embodiments the method can further include applying a first tension to the at least one adjustable limb in a first direction, away from the implant, applying a force to the shuttle filament in a second, opposite direction, toward the implant, thereby causing the shuttle filament to bunch, and then cutting the shuttle filament and the at least one adjustable limb at a location that is proximate to a location at which the terminal end of the adjustable limb exits the shuttle filament. The methods can also include removing the shuttle filament and the cut portion of the at least one adjustable limb from the surgical site.

BRIEF DESCRIPTION OF DRAWINGS

This invention will be more fully understood from the following detailed description taken in conjunction with the accompanying drawings, in which:

FIG. 1 is a perspective view of one exemplary embodiment of a surgical implant, including a cortical button, an adjustable filament loop, a shuttle suture, and a trailing suture;

FIG. 2A is a top perspective view of the cortical button of FIG. 1;

FIG. 2B is an end elevational view of the cortical button of FIG. 2A;

FIG. 2C is a side elevational view of the cortical button of FIG. 2A;

FIGS. 8B-8H are schematic, sequential views illustrating one exemplary embodiment for implanting a graft in a bone tunnel using a schematic surgical implant intended to represent the implant of FIG. 8A.

DETAILED DESCRIPTION

Figure 3:
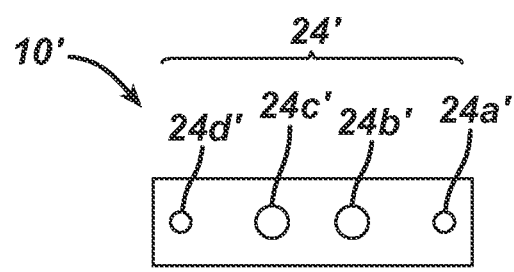
FIG. 3 is a top view of another exemplary embodiment of a cortical button for use as part of a surgical implant.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Further, to the extent arrows are used to describe a direction a component can be tensioned or pulled, these arrows are illustrative and in no way limit the direction the respective component can be tensioned or pulled. A person skilled in the art will recognize other ways and directions for creating the desired tension or movement. Likewise, while in some embodiments movement of one component is described with respect to another, a person skilled in the art will recognize that other movements are possible. Additionally, a number of terms may be used throughout the disclosure interchangeably but will be understood by a person skilled in the art. By way of non-limiting example, the terms "suture" and "filament" may be used interchangeably.

The present disclosure generally relates to a surgical implant for use in surgical procedures such as soft tissue (e.g., ACL) repairs. One exemplary embodiment of such an implant 100 is illustrated in FIG. 1. As shown, the implant 100 can include a body 10 having thru-holes 24 formed therein and at least two suture filaments 40, 60 associated therewith. A first filament 40, sometimes referred to herein as a graft-holding suture, can be coupled to or otherwise associated with the body 10 and configured to hold a graft ligament for implantation. In the illustrated embodiment, a portion of the first filament 40 is formed into an adjustable loop 42 defined by a self-locking knot 46 disposed on a top side 10a of the body 10 and a plurality of coils 42a, 42b, 42c, 42d primarily disposed on a bottom side 10b of the body 10.

The filament 40 can include first and second adjustable limbs 52, 54, which can sometimes be referred to as adjustable tails, extending from the knot 46, and the limbs 52, 54 can be operable to adjust a size of one or more openings 44 formed by one or more of the coils 42a, 42b, 42c, 42d.

A second filament 60, sometimes referred to herein as a shuttle suture or filament or a leading suture or filament, can be removably coupled to or otherwise associated with the body 10 and can be configured to help shuttle the body 10, and thus the first filament 40 and ligament graft associated therewith, into and at least partially through a bone tunnel. As shown, the second filament 60 can have a first limb 62 and a second limb 64 extending from opposed sides of one of the thru-holes 24. Each limb 62, 64 can include a receiving portion 66, 68 configured to receive respective portions of the first and second adjustable limbs 52, 54, thereby assisting in filament management, as well as providing a convenient way to help insure that any cutting of the first and second adjustable limbs 52, 54 is not to the detriment of the integrity of the self-locking knot 46, as discussed in greater detail below.

Optionally, a third filament 80, sometimes referred to herein as a trailing suture or filament, can be removably coupled to or otherwise associated with the body 10 and can be used in conjunction with the second filament 60 to assist in the placement of the body 10 with respect to the bone during a procedure. The third filament 80 can have a first limb 82 and a second limb 84 extending from opposed sides of one of the thru-holes 24.

A body 10 for use as a part of a surgical implant to fixate a ligament graft in bone is illustrated in FIGS. 2A-2C. The body 10 can have a somewhat rectangular, elongate shape with curved leading and trailing terminal ends 16, 18. A plurality of thru-holes 24 can extend from a first, top surface 20 and through a second, bottom surface 22. In the illustrated embodiment there are two outer thru-holes 24a, 24d disposed, respectively, adjacent to leading and trailing terminal ends 16, 18, and two inner thru-holes 24b, 24c disposed between the two outer holes 24a, 24d. As shown, the outer and inner thru-holes 24a, 24d and 24b, 24c have diameters that are substantially the same, and a space separating adjacent thru-holes 24 is substantially the same for each adjacent pair. A width W of the body 10 is defined by the distance between the two elongate sidewalls 12, 14, as shown in FIG. 2B, a length L of the body 10 is defined by the distance between central portions 16c, 18c of the end walls of the leading and trailing terminal ends 16, 18, as shown in FIG. 2C, and a thickness T of the body 10 is defined by the distance between the top and bottom surfaces 20, 22, as shown in FIGS. 2B and 2C. The body 10 can generally be referred to as a cortical button, among other known terms.

A person skilled in the art will recognize that the body 10 described herein is merely one example of a body that can be used in conjunction with the teachings provided herein. A body configured to be associated with a suture filament of the type described herein can have a variety of different shapes, sizes, and features, and can be made of a variety of different materials, depending, at least in part, on the other components with which it is used, such as the suture filament and the ligament graft, and the type of procedure in which it is used. Thus, while in one embodiment the body 10 is somewhat rectangular having curved ends, in other embodiments the body can be substantially tubular, among other shapes.

In one exemplary embodiment of the substantially rectangular body 10, the length L of the body is in the range of about 5 millimeters to about 30 millimeters, the width W is in the range of about 1 millimeter to about 10 millimeters, and the thickness T is in the range of about 0.25 millimeters to about 3 millimeters. In one exemplary embodiment, the length L can be about 12 millimeters, the width W can be about 4 millimeters, and the thickness T can be about 1.5 millimeters. Diameters of the thru-holes 24 can be in the range of about 0.5 millimeters to about 5 millimeters, and in one exemplary embodiment each can be about 2 millimeters. Although in the illustrated embodiment each of the thru-holes 24a, 24b, 24c, 24d has a substantially similar diameter, in other embodiments some of the thru-holes can have different diameters, such as thru-holes 24a', 24b', 24c', 24d' of body 10' illustrated in FIG. 3. Likewise, although in the illustrated embodiment of FIGS. 2A-2C the thru-holes 24a, 24b, 24c, 24d are approximately equally spaced apart with respect to each other, in other embodiments some or all of the thru-holes can be spaced apart by unequal amounts, as also illustrated by the thru-holes 24a', 24b', 24c', 24d' of FIG. 3. Additionally, any number of thru-holes can be formed in the body 10, including as few as two.

In exemplary embodiments the body 10 can be made from a stainless steel or titanium, but any number of polymers, metals, or other biocompatible materials in general can be used to form the body. Some non-limiting examples of biocompatible materials suitable for forming the body include a polyether ether ketone (PEEK), bioabsorbable elastomers, copolymers such as polylactic acid-polyglycolic acid (PLA-PGA), and bioabsorbable polymers such as polylactic acid. The implant can also be formed of absorbable and non-absorbable materials. Other exemplary embodiments of a body or cortical button that can be used in conjunction with the teachings herein are described at least in U.S. Pat. No. 5,306,301 of Graf et al., the content of which is incorporated by reference herein in its entirety.

Figure 4:
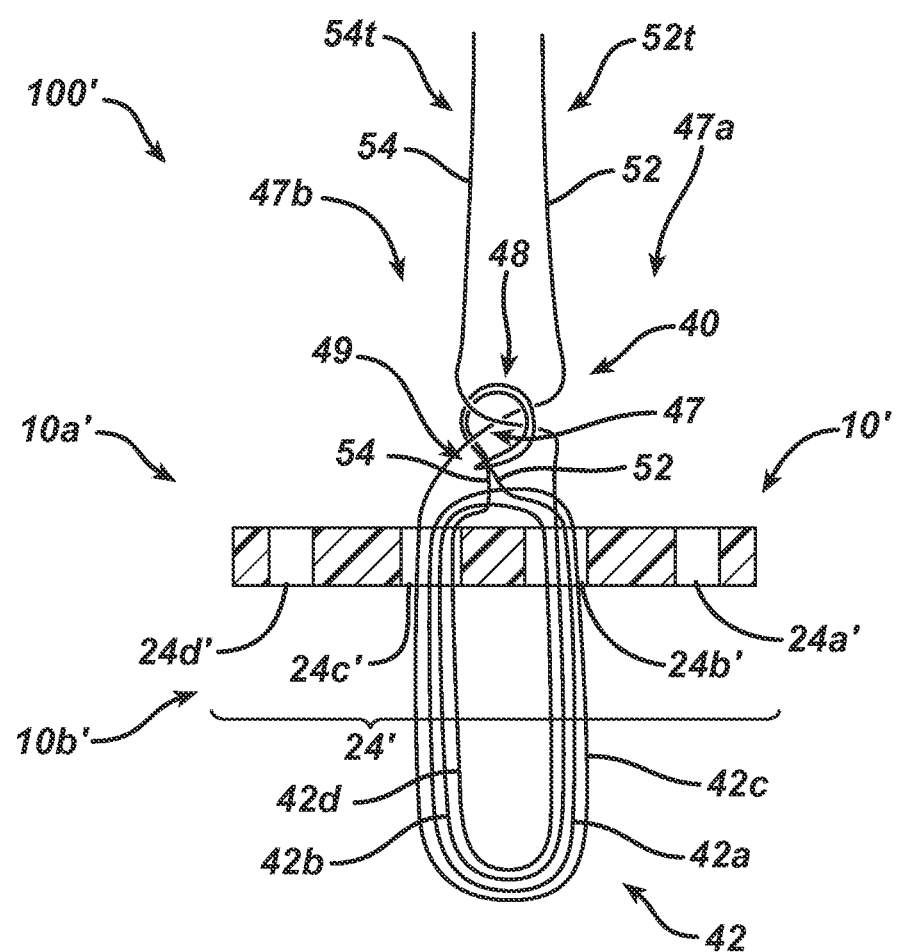
FIG. 4 is a schematic side cross-sectional view of the cortical button of FIG. 3 having an adjustable filament loop associated therewith to form a surgical implant.

The first filament 40 can be associated with the body 10, 10' to form a surgical implant 100, 100' in a variety of ways. As shown in FIG. 4, the first filament 40 can be formed into a Lark's Head knot configuration 48 that forms an opening 47. The Lark's Head knot configuration 48, in turn, can be collapsed as described below to form a sliding knot 46 on a top side 10a' of the body 10'. The collapsed knot 46 formed on a top side 10a' of a body 10' is shown at least in FIG. 1 herein. A person skilled in the art will understand numerous techniques that can be used to form the Lark's Head knot configuration 48, and thus further discussion of its formation is unnecessary. Further, although in the illustrated embodiment the collapsed knot 46 is formed on the top side 10a' of the body 10', in other embodiments the knot 46 can be configured to be located at other locations with respect to the body 10', for example a bottom side 10b' of the body 10'.

The adjustable limbs 52, 54 can extend distally beyond the opening, as shown in FIG. 4, toward the body 10', after passing a folded end 49 of the configuration 48, and each limb 52, 54 can be selectively passed through multiple thru-holes 24' of the body 10' to associate the filament 40 with the body 10'. In the illustrated embodiment, the first limb 52 passes distally through the second hole 24b' to the bottom side 10b' of the body 10', and through the third thru-hole 24c' back to the top side 10a' twice to form a first coil 42a and a second coil 42c before it is then passed through the opening 47 from a second side 47b of the opening 47 to a first side 47a. Similarly, the second limb 54 passes distally through the third hole 24c' to the bottom side 10b', and through the second thru-hole 24b' back to the top side 10a' twice to form a first coil 42b and a second coil 42d before it is then passed through the opening 47 from the first side 47a to the second side 47b. The opening 47 can be collapsed, and a circumference of the first and second coils 42a, 42c can be adjusted by terminal end 52t of the first limb 52 and the first and second coils 42b, 42d can be adjusted by terminal end 54t of the second limb 54.

Any number of coils can be formed from the first and second limbs 52, 54, including a single coil from each, and the number of coils formed in the first limb 52 does not have to be the same number of coils formed in the second limb 54. In some exemplary embodiments, three or four coils can be formed in one or both of the limbs. Further, the limbs used to form the coils can be passed through any number of thru-holes formed in the body 10'. The first limb 52 does not need to pass through the same thru-holes through which the second limb 54 passes, and likewise, when multiple coils are formed in one limb, that limb does not have to be passed through the same thru-holes to form each coil. A person skilled in the art will recognize a number of configurations between the filament and thru-holes that can be used to form one or more coils in the filament limbs before disposing terminal ends of the limbs through a collapsible opening of a knot to create a self-locking knot.

Figure 5A:
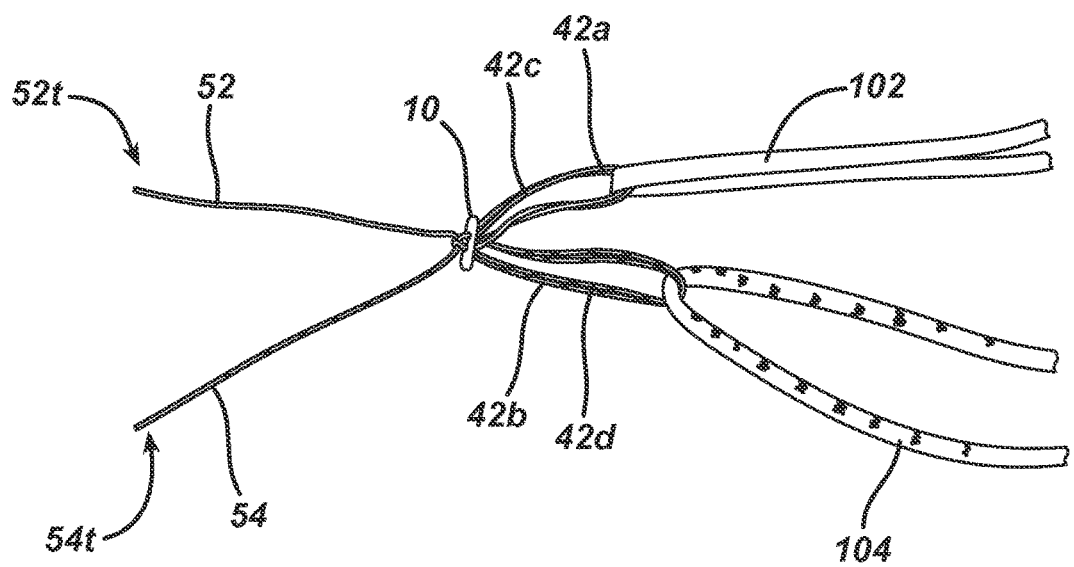
FIGS. 5A-5B are sequential views of the surgical implant of FIG. 4, the implant having grafts associated therewith, illustrating selective movement of the grafts.
Figure 5B:
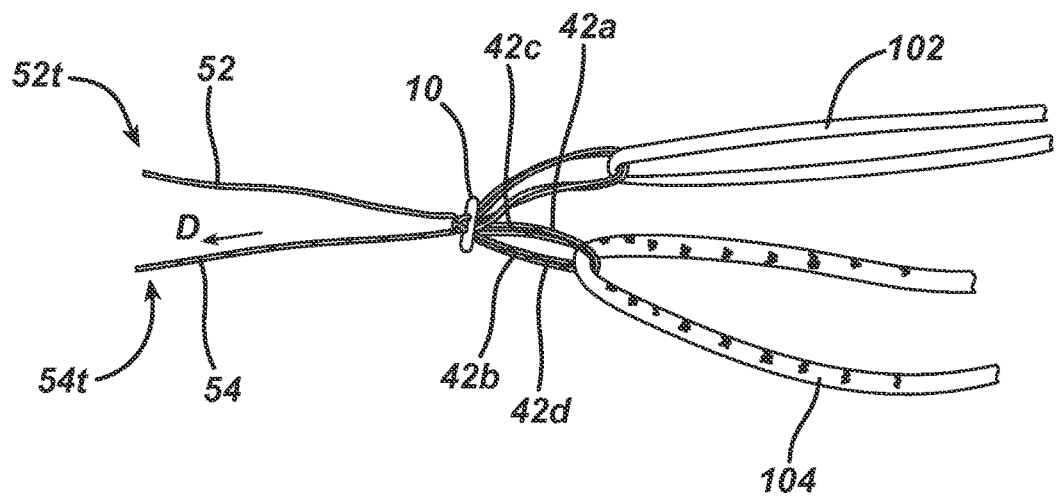

The configuration of the body 10, 10' and the first filament 40 can allow for selective movement of the coils 42a, 42b, 42c, 42d, and thus grafts 102, 104 associated therewith, as illustrated in FIGS. 5A and 5B. As shown, a first ligament graft 102 is coupled to first and second coils 42a, 42c of the first limb 52 by wrapping the graft 102 through each of the first and second coils 42a, 42c, and a second ligament graft 104 is coupled to first and second coils 42b, 42d of the second limb 54 by wrapping the graft 104 through each of the first and second coils 42b, 42d. Applying a force to the second limb 54 in an approximate direction D decreases the circumference of the first and second coils 42b, 42d, thereby drawing the second ligament graft 104 closer to the body 10. More particularly, as tension is created by the force, the circumference of the diameter of the second coil 42d decreases and advances the second graft 104. As the distance between distal ends of the second coil 42d and the first coil 42b increases, the weight of the graft 104 helps create a counterforce that maintains the circumference of the second coil diameter while the circumference of the first coil 42b decreases to catch-up to the second coil 42d and the graft 104. A person skilled in the art will understand how the application of various forces and tensions to the first and second limbs 52, 54, the first and second coils 42a, 42c and 42b, 42d, and the first and second grafts 102, 104 associated therewith can be manipulated to selectively adjust locations of the grafts 102, 104 with respect to the body 10, 10'.

The first filament 40 can be an elongate filament, and a variety of different types of suture filaments can be used, including but not limited to a cannulated filament, a braided filament, and a mono filament. The type, size, and strength of the filament can depend, at least in part, on the other materials of the implant, including the material(s) of the cortical button and the ligament graft, the tissue, bone, and related tunnels through which it will be passed, and the type of procedure in which it is used. In one exemplary embodiment the filament is a #0 filament (about 26 gauge to about 27 gauge), such as an Orthocord™ filament that is commercially available from DePuy Mitek, LLC., 325 Paramount Drive, Raynham, Mass. 02767, or an Ethibond™ filament that is commercially available from Ethicon, Inc., Route 22 West, Somerville, N.J. 08876. The thickness of the filament should provide strength in the connection but at the same time minimize the trauma caused to tissue through which it passes. In some embodiments the filament can have a size in the range of about a #5 filament (about 20 gauge to about 21 gauge) to about a #3-0 filament (about 29 gauge to about 32 gauge). Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed. In some exemplary embodiments, a length of the filament can be in the range of about 0.2 meters to about 5 meters, and in one embodiment it has a length of about 1.5 meters.

The first filament 40 can be delivered to a surgeon for use pre-attached to the cortical button. Alternatively, the formation of the loop 42 can be performed by a surgeon prior to inserting the implant 100, 100' into a bone tunnel. The surgeon can use any of the techniques described herein, or otherwise known to those skilled in the art to couple to first filament 40 to a cortical button.

Figure 6:
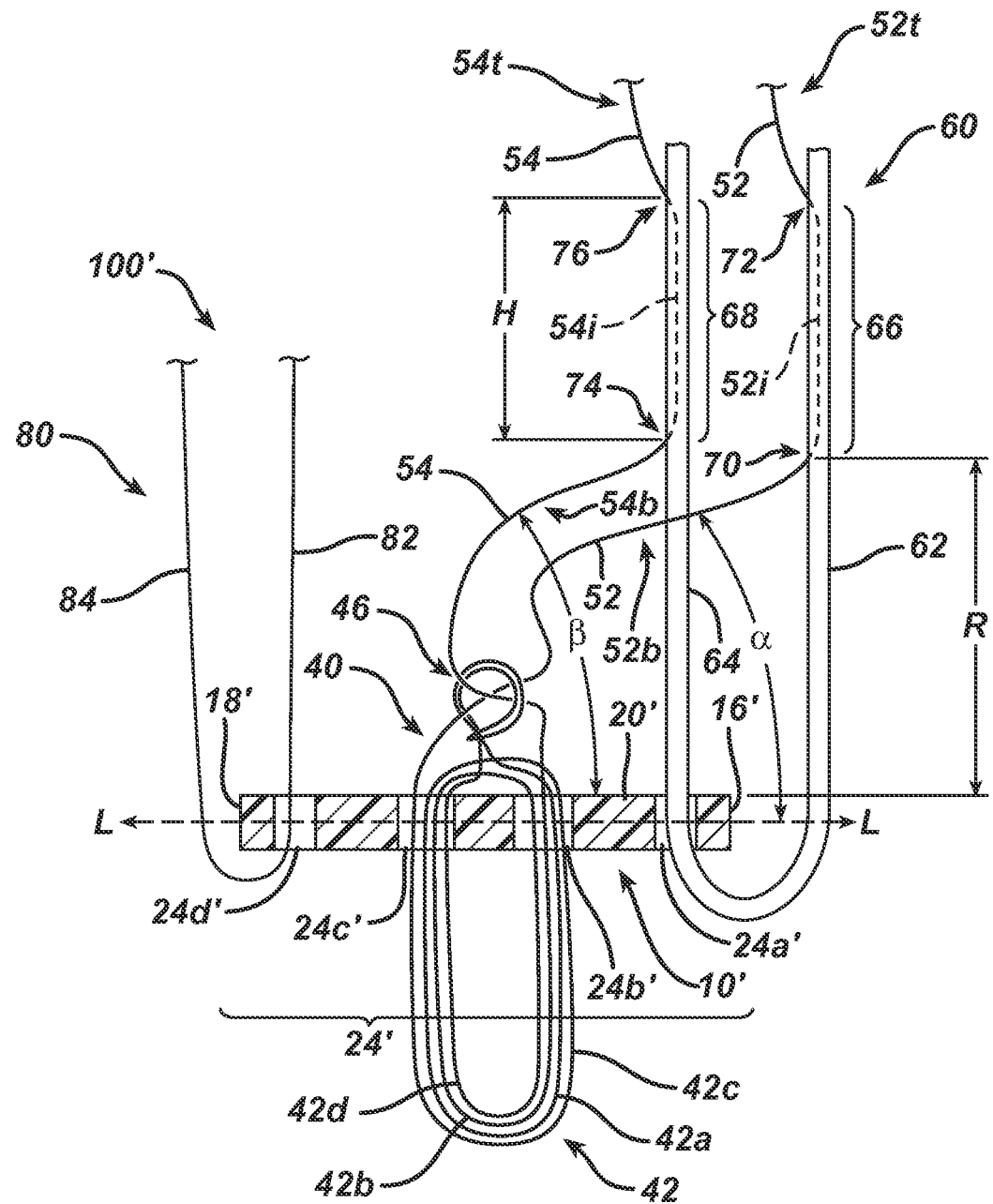
FIG. 6 is a schematic cross-sectional view of the surgical implant of FIG. 4, including the cortical button, the adjustable filament loop, a shuttle suture, and a trailing suture.

FIG. 6 illustrates the inclusion of both a shuttle or leading suture 60 and a trailing suture 80 with the body 10' of the implant 100'. As shown, the shuttle suture 60 can be disposed through the thru-hole 24a' and around a leading end 16' of the body 10' such that opposed first and second limbs 62, 64 extend proximally from the body 10'. The first limb 62 can include a receiving portion 66, and the second limb 64 can likewise include a receiving portion 68. The receiving portions 66, 68 can be configured to receive a portion of the filament limbs 52, 54, respectively, to serve as a sleeve or guard for the limbs 52, 54. In the illustrated embodiment, the receiving portions 66, 68 include a portion of the shuttle suture 60 that is hollow. For example, portions of the core of filament 60 can be removed using techniques known to those skilled in the art. Likewise, other techniques known for forming hollow sections in a filament can be used, including but not limited to using a shuttle suture having a reduced pick count, as described further below. Accordingly, to the extent the term "hollow portion" is used to describe a portion of the configuration of the shuttle suture, it does not limit the shuttle suture to actually being hollow, and thus can include other configurations that allow the hollow portion to receive the limbs 52, 54, e.g., a reduced pick count and/or looser braid.

Openings 70, 72 and 74, 76 can be formed in the shuttle suture 60 to access the hollow portions. As shown, second openings 72, 76, through which limbs 52, 54 can exit the receiving portions 66, 68, can be located more remote from the body 10' than first openings 70, 74, through which the limbs 52, 54 can enter the receiving portions 66, 68. Openings 70, 72 and 74, 76 can be located at any distance proximal of the body 10'. For example, a vertical distance R between a top surface 20' of the body 10' and the first openings 70, 74 can be approximately in the range of about 5 millimeters to about 50 millimeters, and in one exemplary embodiment the distance R can be about 10 millimeters. As the vertical distance increases, it can be easier for the shuttle suture 60 to be removed from the body 10' once a procedure is completed and the shuttle suture 60 is no longer needed. Further, a length H of the hollow portion can be approximately in the range of about 10 millimeters to about 100 millimeters, and in one exemplary embodiment the length H can be about 20 millimeters. The length H of the hollow portion can approximately reflect the length of the limbs 52, 54 that remain after a portion of the limbs 52, 54 are cut and removed, as discussed below.

The limbs 52, 54 can be associated with the receiving portions 66, 68 of the shuttle suture 60 by extending terminal ends 52t, 54t of the limbs 52, 54 from the knot 46 (shown in its un-collapsed, Lark's Head configuration 48 in FIG. 6) and toward the shuttle suture 60. As shown, body-facing surfaces 52b, 54b of the limbs 52, 54 can form acute angles α, β, respectively, with a longitudinal axis L extending through the length of the implant body 10'. The terminal ends 52t, 54t can be passed through the first openings 70, 74 of the shuttle suture 60, through the hollow, receiving portions 66, 68, and then out the second openings 72, 76 such that an intermediate portion 52i, 54i of each of the limbs 52, 54 is disposed in the receiving portions 66, 68. In other embodiments, for instance where the shuttle suture 60 is a braided suture, openings resulting from the braided configuration can be used to dispose the limbs 52, 54 in the shuttle suture 60. Still further, the limbs 52, 54 can be associated with the shuttle suture 60 in a variety of other ways that still allow the limbs 52, 54 and shuttle suture 60 to be moved through bone tunnels concurrently while still allowing the limbs 52, 54 to adjust the loop 42. By way of non-limiting example, the limbs 52, 54 can be weaved through the shuttle suture 60 one or more times at the identified receiving portions 66, 68.

The shuttle suture 60 can be an elongate filament of a variety of types, including but not limited to a cannulated filament and a braided filament. The type, size, and strength of the filament can depend, at least in part, on the other materials of the implant, such as the cortical button and the first, graft-holding filament, and the type of procedure in which it is used. The shuttle suture 60 can be made from a wide variety of biocompatible flexible materials, including a flexible polymer. In one embodiment the shuttle suture 60 is made of a polymeric material having a core disposed therein. As described above, at least a portion of the core can be removed to provide one or more receiving portions 66, 68. In another embodiment, the shuttle suture is a flexible filament, such as a braided suture, for example Ethibond™ #5 filament (about 20 gauge to about 21 gauge). In some exemplary embodiments, the shuttle suture can be a #5 braided, flexible filament (about 20 gauge to about 21 gauge) and can be made of ultra high molecular weight polyethylene with two polyester racers. The pick count of the braid can adjusted as desired. For example, the pick count can be approximately in the range of about 30 picks per 2.54 centimeters to about 80 picks per 2.54 centimeters, and in one instance the pick count can be about 36 picks per 2.54 centimeters. A person skilled in the art will recognize that other pick counts can be used depending, at least in part, on the size of the filament to be received by the shuttle suture, the type of tissue through which the shuttle suture will be disposed, and the various desired properties of the overall construct, such as the ease of sliding a filament within the shuttle suture and/or the amount of bunching that is desired in the shuttle suture. A length of the shuttle suture can be in the range of about 0.1 meters to about 1.5 meters, and in one embodiment the length is about 1 meter.

Although the illustrated embodiment shows the loop 42 formed by the first filament 40 having two limbs 52, 54 extending from the knot 46 (i.e., the Lark's Head knot configuration 48), in some embodiments, a single adjustable limb can extend from the knot. Accordingly, the shuttle suture 60 can have a single receiving portion that is hollow, and a portion of the single adjustable limb can be disposed in the hollow portion. Alternatively, if two adjustable limbs are included, both can be disposed in the same receiving portion. In other embodiments, three or more adjustable limbs can extend from the loop formed by the first filament, and the shuttle suture can be configured to receive any number of the limbs, including more than two, without departing from the spirit of the present disclosure.

The trailing suture 80 can optionally be included to further assist passing the implant 100' through a bone tunnel, as described in further detail below. As shown, the trailing suture 80 can be disposed through the thru-hole 24*d* and around a trailing end 18' of the body 10' such that opposed first and second limbs 82, 84 extend proximally from the body 10'. Similar to other filaments of the present disclosure, the trailing suture can be an elongate filament of a variety of types, including but not limited to a cannulated filament, a braided filament, and a mono filament. The type, size, and strength of the filament can depend, at least in part, on the other materials of the implant, such as the cortical button, and the type of procedure in which it is used. In one exemplary embodiment the trailing suture is formed from a #5 filament (about 20 gauge to about 21 gauge). In some embodiments the filament can have a size in the range of about a #2-0 filament (about 28 gauge) and about a #5 filament (about 20 gauge to about 21 gauge). A length of the filament can be in the range of about 0.1 meters to about 1.5 meters, and in one embodiment the length is about 1 meter.

Both the shuttle or leading filament 60 and the trailing filament 80 can be removably coupled to the body 10'. In some embodiments, the action of associating either or both of the leading filament 60 and the trailing filament 80 with the body 10' by passing the filaments through thru-holes 24' of the body 10' can be performed by a surgeon during a procedure. In some other embodiments, the body 10' can come pre-loaded with either or both of the leading filament 60 and the trailing filament 80 already passed through the respective thru-holes 24' of the body 10'. The filaments 60, 80 may have a loose knot formed therein to help maintain their location in the thru-holes 24' during shipping, and then the knot can be undone once removed from the packaging. Other techniques use to maintain an approximate location of a filament with respect to a cortical button during shipping can also be used in conjunction with the body 10', leading filament 60, and trailing filament 80 without departing from the spirit of the present disclosure.

Although the embodiment illustrated in FIG. 6 shows each of the leading filament 60 and the trailing filament 80 extending through different thru-holes 24' than the thru-holes 24' through which the coils 42*a'*, 42*b'*, 42*c'*, 42*d'* are formed, in other embodiments either or both of the leading filament 60 and the trailing filament 80 can use one or more of the same thru-holes 24' as the filament 40 used to form the coils 42*a'*, 42*b'*, 42*c'*, 42*d'* and/or the other of the leading and trailing filaments 60, 80. Further, although the illustrated embodiment shows the leading filament 60 and the trailing filament 80 disposed in thru-holes 24' of the body 10', a person skilled in the art will recognize other ways by which the filaments 60, 80 can be associated with the body 10', including, by way of non-limiting example, by wrapping one or both of the filaments 60, 80 around the body 10'. Other techniques for associating either or both of the filaments 60, 80 with the body 10' do not depart from the spirit of the present disclosure. Additionally exemplary embodiments of implants that can include cortical buttons, graft-holding filaments, leading filaments, and/or trailing filaments are provided at least in U.S. patent application Ser. No. 13/793,514, filed Mar. 11, 2013, and entitled "Implant Having Adjustable Filament Coils," the content of which is incorporated by reference herein in its entirety.

Figure 7A:
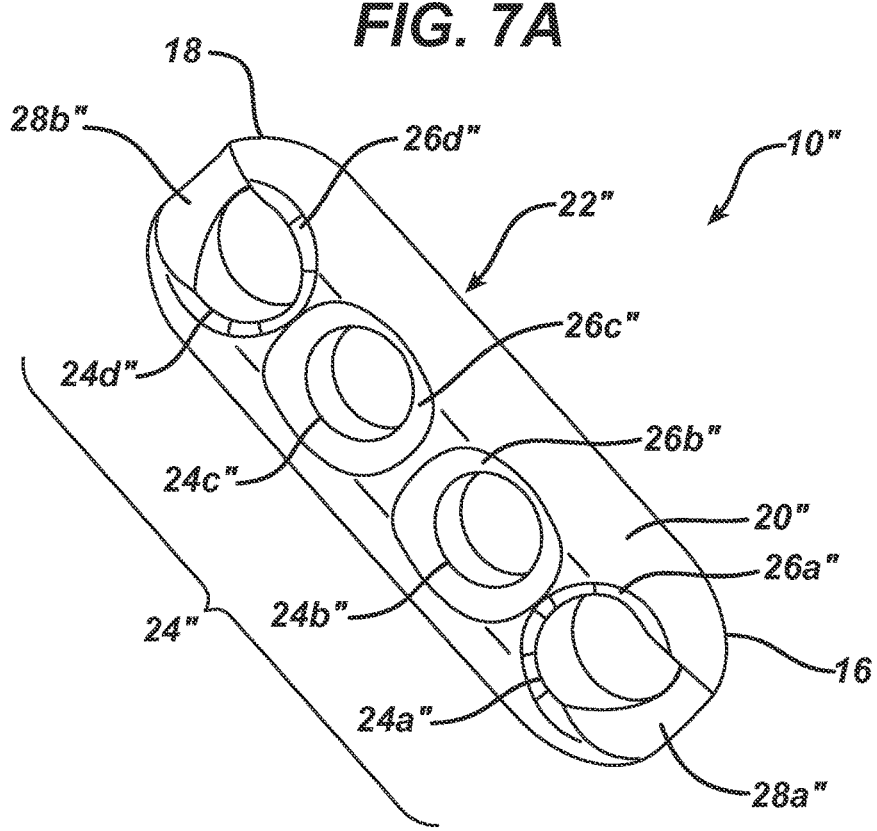
FIG. 7A is a perspective view of another exemplary embodiment of a cortical button for use as a surgical implant.
Figure 7B:
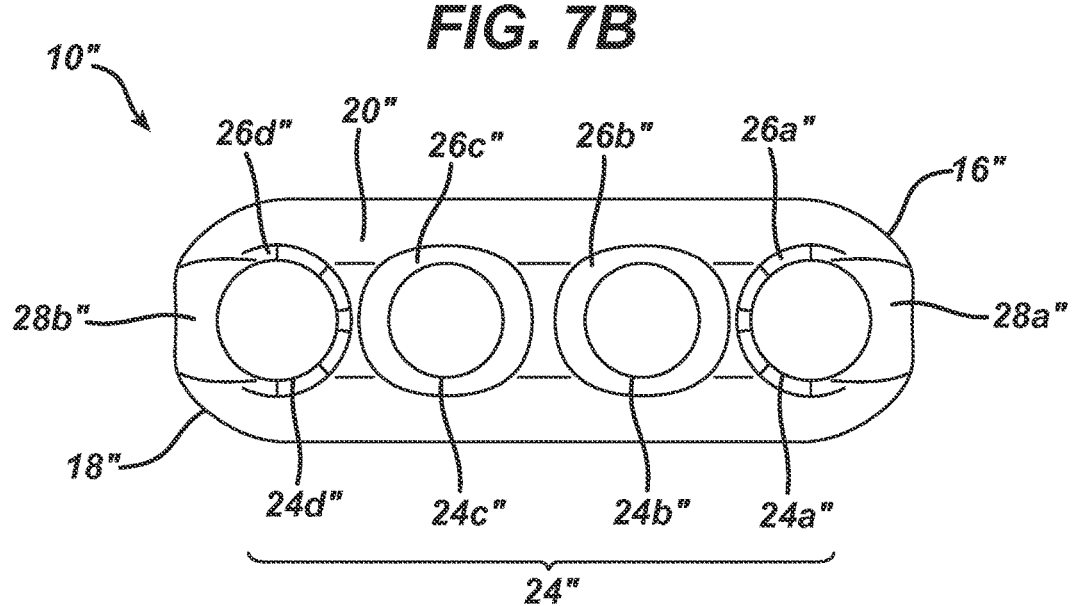
FIG. 7B is a top view of the cortical button of FIG. 7A.

FIGS. 7A and 7B illustrate an alternative embodiment of an implant body 10''' that is configured to assist in removing the leading filament 60 from an implant 100''' following the conclusion of a procedure. Similar to the body of FIGS. 2A-2C, the body 10''' has a somewhat rectangular, elongate shape with curved leading and trailing terminal ends 16''', 18''', and a plurality of thru-holes 24''' extending from a top surface 20''' and through a second, bottom surface 22'''. As shown, each of the thru-holes 24*a'''*, 24*b'''*, 24*c'''*, 24*d'''* has a substantially similar diameter and each includes a chamfered edge 26*a'''*, 26*b'''*, 26*c'''*, 26*d'''* to help reduce fraying of filaments disposed therethrough. Further, the body 10''' can include one or more notches formed therein, as shown two notches 28*a'''*, 28*b'''*, each adjacent to respective outer thru-holes 24*a'''*, 24*d'''*. The notches 28*a'''*, 28*b'''* can be formed by removing a rounded portion of the body 10''', thereby providing a smooth, thinner surface through which filaments such as the leading filament 60 and the trailing filament 80 can be disposed. The notches 28*a'''*, 28*b'''* can help prevent possible fraying of filaments disposed in the implant 100''', and can also make it easier to disassociate filaments disposed in the outer thru-holes 24*a'''*, 24*d'''* from the body 10''' by providing a surface that reduces friction and the likelihood of the filament getting caught by or otherwise stuck to a portion of the body 10'''.

Figure 8A:
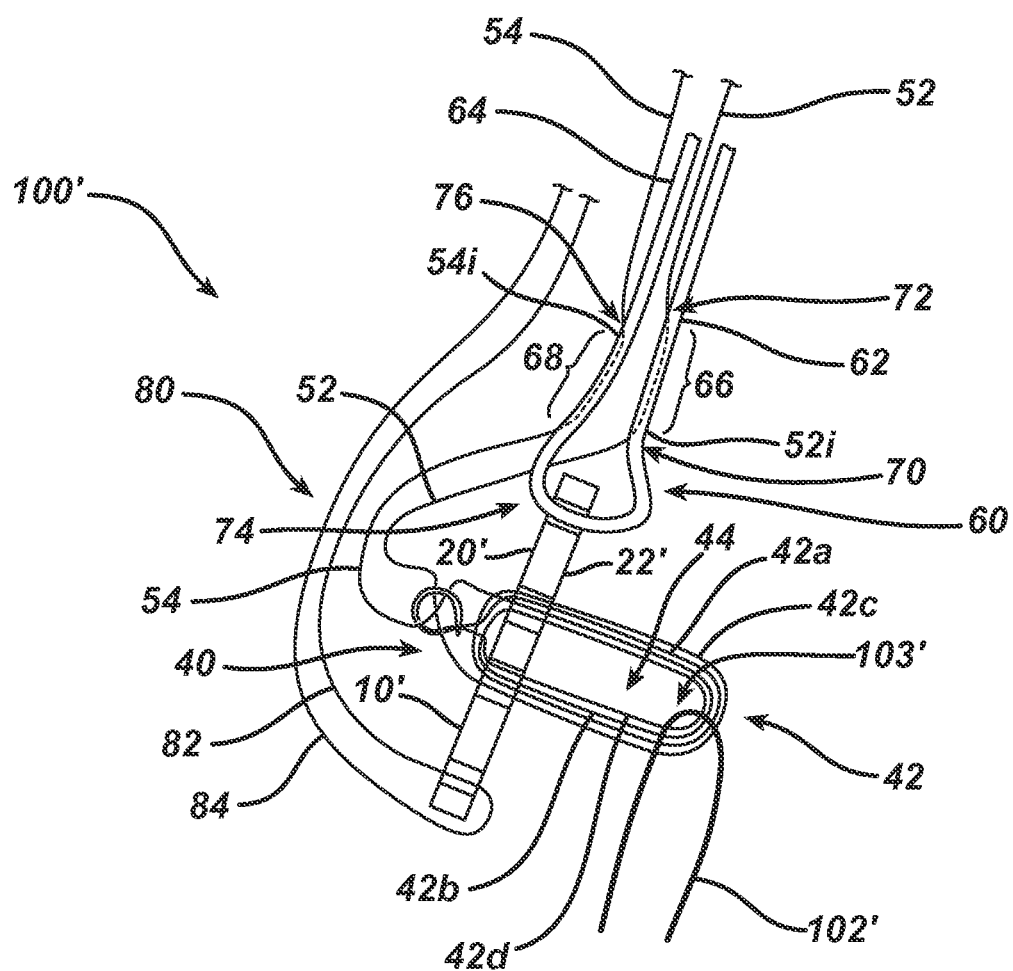
FIG. 8A is a schematic, detailed view of the surgical implant of FIG. 6 oriented to pass through a bone tunnel and having a graft associated therewith.

Different exemplary features associated with performing soft tissue repair (e.g., an ACL repair) using a surgical implant like those described herein are illustrated in FIGS. 8A-8H. As shown in FIG. 8A, the implant 100' of FIG. 6 is oriented at an angle approximately commensurate with an angle of a bone tunnel formed in bone, as described in further detail below. A graft ligament 102' is coupled to at least one of the coils 42*a*, 42*b*, 42*c*, 42*d* of the adjustable loop 42 by disposing a folded end 103' of the graft ligament 102' through openings 44 of the coils 42*a*, 42*b*, 42*c*, 42*d*. Although in the illustrated embodiment the graft ligament 102' is disposed through openings 44 of all four coils 42*a*, 42*b*, 42*c*, 42*d*, less than all, and even one, coil can be associated with one graft ligament 102' while one or more other coils are associated with one or more other graft ligaments. In some embodiments multiple grafts can be associated with the same coil. The grafts can be associated with any of the coils using any techniques known to those skilled in the art.

The implant 100''' illustrated in FIGS. 8B-8G is a schematic representation of the implant 100' of FIG. 8A. Thus, the coils 42*a*, 42*b*, 42*c*, 42*d* are generally illustrated as a single loop 42', and the filament limbs 52, 54 are generally illustrated as a single adjustment limb 53'. Likewise, the two limbs 62, 64 of the leading filament 60 are generally illustrated as a leading filament or shuttle suture 60' having a single limb, and the two limbs 82, 84 of the trailing filament 80 are generally illustrated as a trailing filament or suture 80' having a single limb. This schematic representation makes it easier to see the various components of the implant 100''' disposed in the bone tunnel, and based on the disclosures herein, it is easy to adapt different numbers of filaments and limbs for use in the methods described herein. Further, although the inclusion of a single loop 42' and a single adjustment limb 53' are described as a schematic representation of components of the implant 100', the disclosures herein make it clear that a single loop and single adjustment limb, as well as a single receiving portion of a leading filament, can be used in conjunction with the devices and methods provided for herein.

Figure 8B:
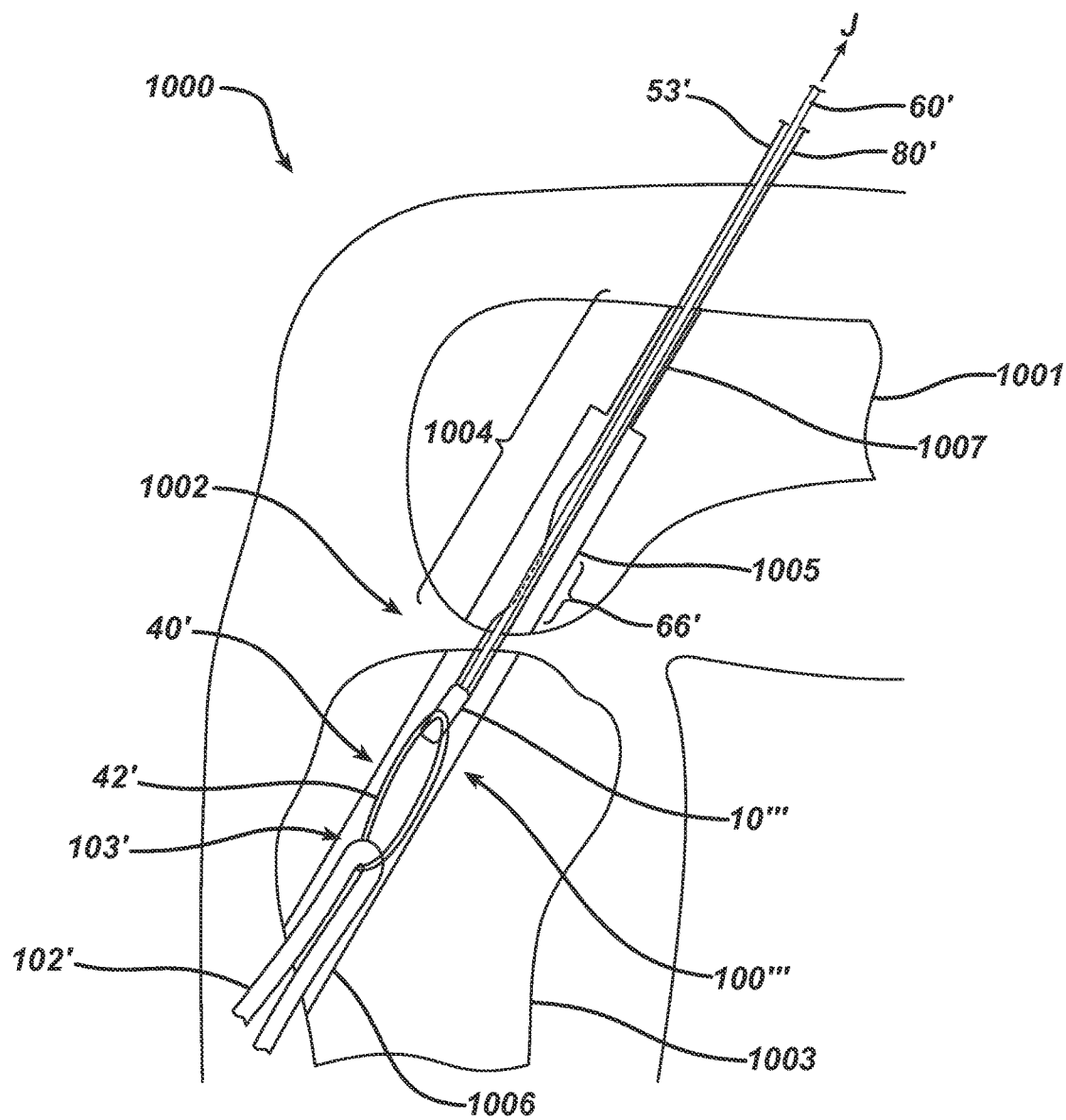

A surgeon can begin the procedure by preparing the knee 1000 and soft tissue tendon grafts using techniques known by those skilled in the art. As shown in FIG. 8B, a bone tunnel 1002 can be formed in a femur 1001 and tibia 1003, with a femoral tunnel 1004 of the bone tunnel 1002 including a main channel 1005 and a passing channel 1007, the passing channel 1007 having a smaller diameter than the main channel 1005, and the femoral tunnel 1004 being in direct communication with a tibial tunnel 1006 disposed in the tibia 1003. The implant 100''' can be introduced into the tibial tunnel 1006 by applying a force in an approximate direction J to the leading and trailing filaments 60', 80', which both extend toward the femoral tunnel 1004 as shown. The adjustable limb 53' can also extend toward the femoral tunnel 1004.

Figure 8C:
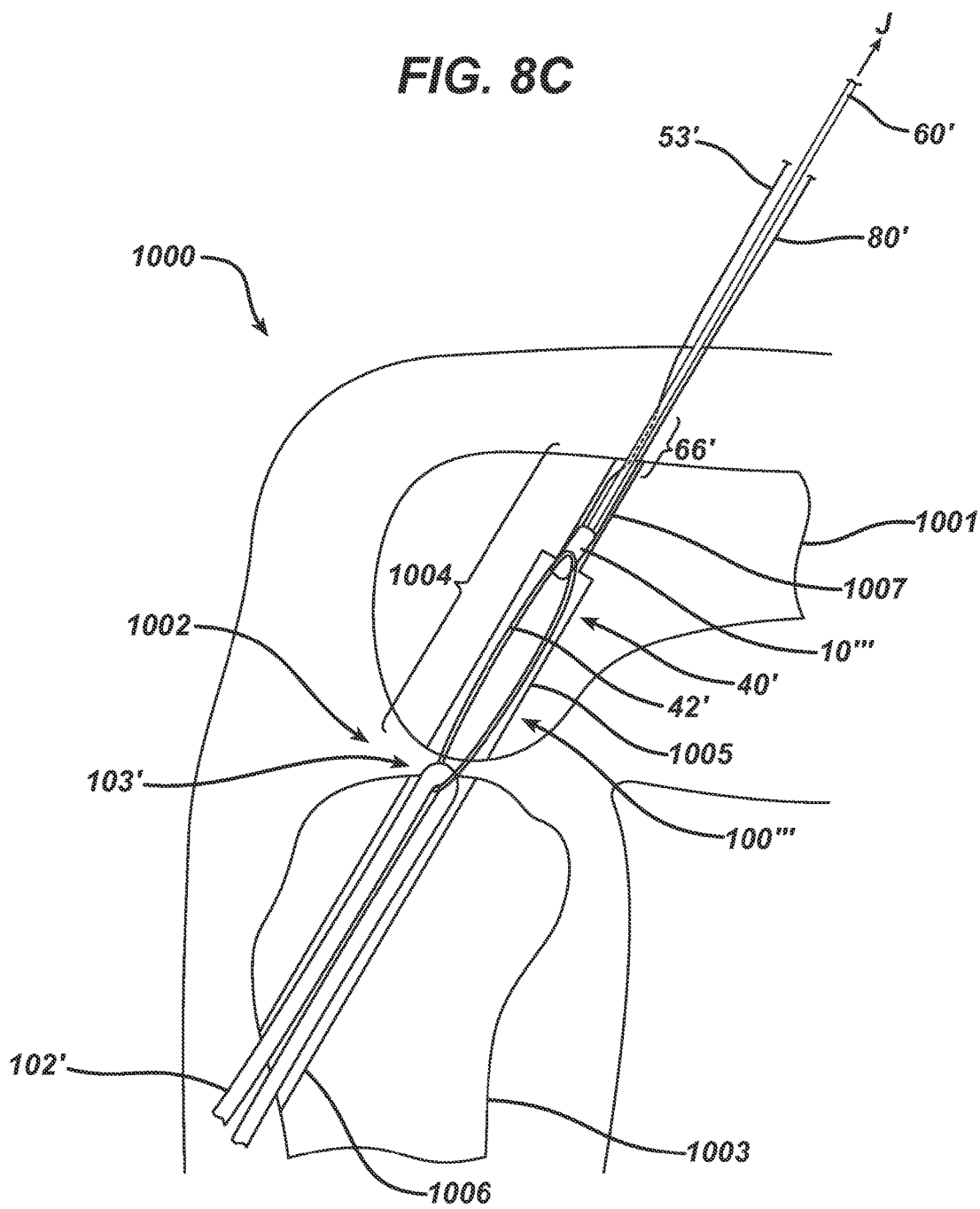
Figure 8F:
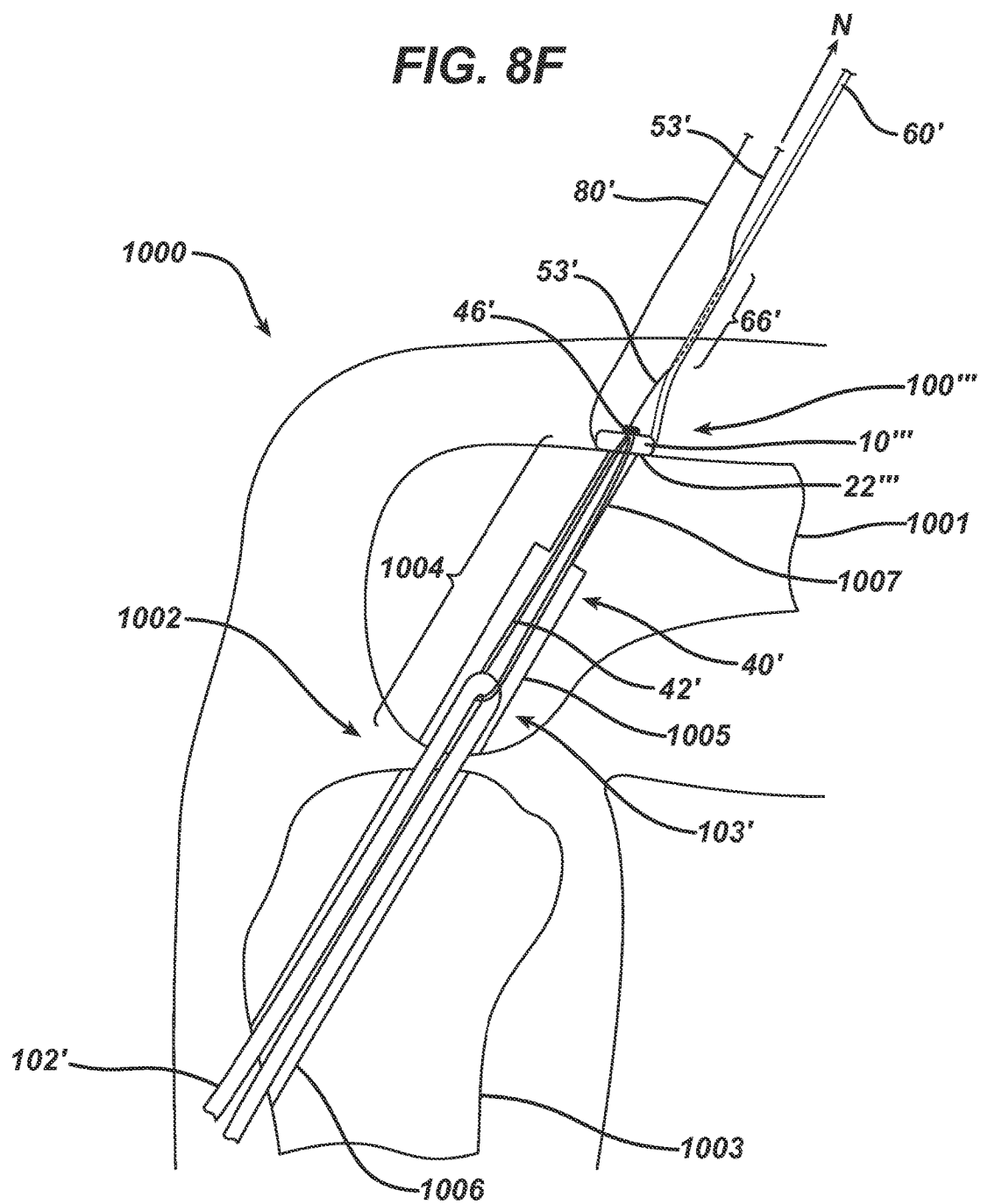

As shown in FIG. 8C, the continued application of the force in the approximate direction J to the leading filament 60' and the trailing filament 80', as well as, optionally, to the adjustable limb 53', can advance the implant 100''' and components associated therewith through the tibial tunnel 1006 and into the femoral tunnel 1004. In the illustrated embodiment, because each filament 53', 60', 80' passing through the bone tunnel 1002 has tension applied to it, the possibility of any filament bunching or otherwise clogging the bone tunnel 1002 is decreased.

A counterforce can be applied to the graft 102' so that the entire construct is not fully inserted into the bone tunnel 1002. This allows for the graft 102' to be used to help orient the body or cortical button 10''' or the implant 100''' with respect to the bone tunnel 1002 if desired. Further, as the button 10''' and loop 42' enter the bone tunnel 1002, care can be taken to prevent the button 10''' from becoming wrapped in one or more coils of the loop 42'. Once the implant 100''' enters the bone tunnel 1002, optical devices, such as arthroscopes, can be used to continue to monitor it. If any one of the coils of the loop 42' undesirably wraps around the button 10''', the surgeon can use instruments to unwrap the coils from the button and/or the surgeon can selectively apply tension to any of the leading filament 60', the trailing filament 80', and the graft 102' to manipulate and untangle the button 10''' from the coil(s).

Continued application of the force in the approximate direction J can pull the cortical button 10''' through the passing channel 1007. As the button 10''' passes through the passing channel 1007 and crests while passing out of the channel, i.e., when a substantial portion of the button 10''' is disposed outside of the channel, as shown in FIG. 8D, the surgeon can prepare to orient or manipulate the button 10''' so that it flips or changes orientation. Because tissue and ligaments can be located near a proximal end of the femoral tunnel 1004, typically when cortical buttons pass out of a femoral tunnel, the extra tissue can make it difficult to direct the button to a desired location. However, the leading and trailing filaments 60', 80' can assist in manipulating the button 10''' to a desired location in which a flat bottom surface 22''' of the body 10''' rests on the femoral cortex and faces the femoral tunnel 1004, as shown in FIG. 8E. This allows the loop 42' and graft 102' associated therewith to be disposed in the bone tunnel 1002 and the knot 46' to be located outside of but adjacent to the bone tunnel 1002. In other embodiments, the button 10''' can be flipped so that a top surface 20''' of the body''' rests on the femoral cortex and faces the femoral tunnel 1004.

A variety of techniques can be used to flip or reorient the cortical button 10''', but in the illustrated embodiment, shown in FIG. 8E, a force in an approximate direction K is applied to the graft 102', thus tensioning the graft 102' and causing the button 10''' to flip. In other embodiments, a surgeon can selectively apply tension to the graft 102' and the leading and trailing filaments 60', 80' to flip the button 10''' to its desired location. Once the surgeon has oriented the button 10''' as desired, the surgeon can confirm its location as lying flat on the femoral cortex, directly adjacent to the femoral tunnel 1004, using a variety of techniques, including by using tactile feedback received from pulling the leading and trailing filaments 60', 80' and the graft 102', and/or using visual aids.

Once the button 10''' is disposed at its desired location, tension can be applied to the adjustable limb 53' to adjust a circumference of the loop 42', thereby moving the graft 102' within the bone tunnel 1002 to a desired location. The circumference of the loop 42', and thus the circumferences of the coils represented by the loop 42', can be adjusted using a number of different techniques, including those described herein. In one exemplary embodiment, illustrated in FIG. 8F, the adjustable limb 53' can be selectively pulled in an approximate direction N to advance the graft 102' through the tunnel 1002.

Once the implant 100''' and graft 102' are positioned in their desired locations, excess filaments can be removed, including portions of the adjustable limb 53', the leading filament 60', and the trailing filament 80'. When cutting excess filament, such as from the adjustable limb 53', care is generally taken to ensure that enough material remains so as not to negatively impact the integrity of the knot 46'. The configuration of the implant 100''', and in particular having a leading filament 60' having a receiving portion 66' for receiving the adjustable limb 53', can help in this regard.

Figure 8G:
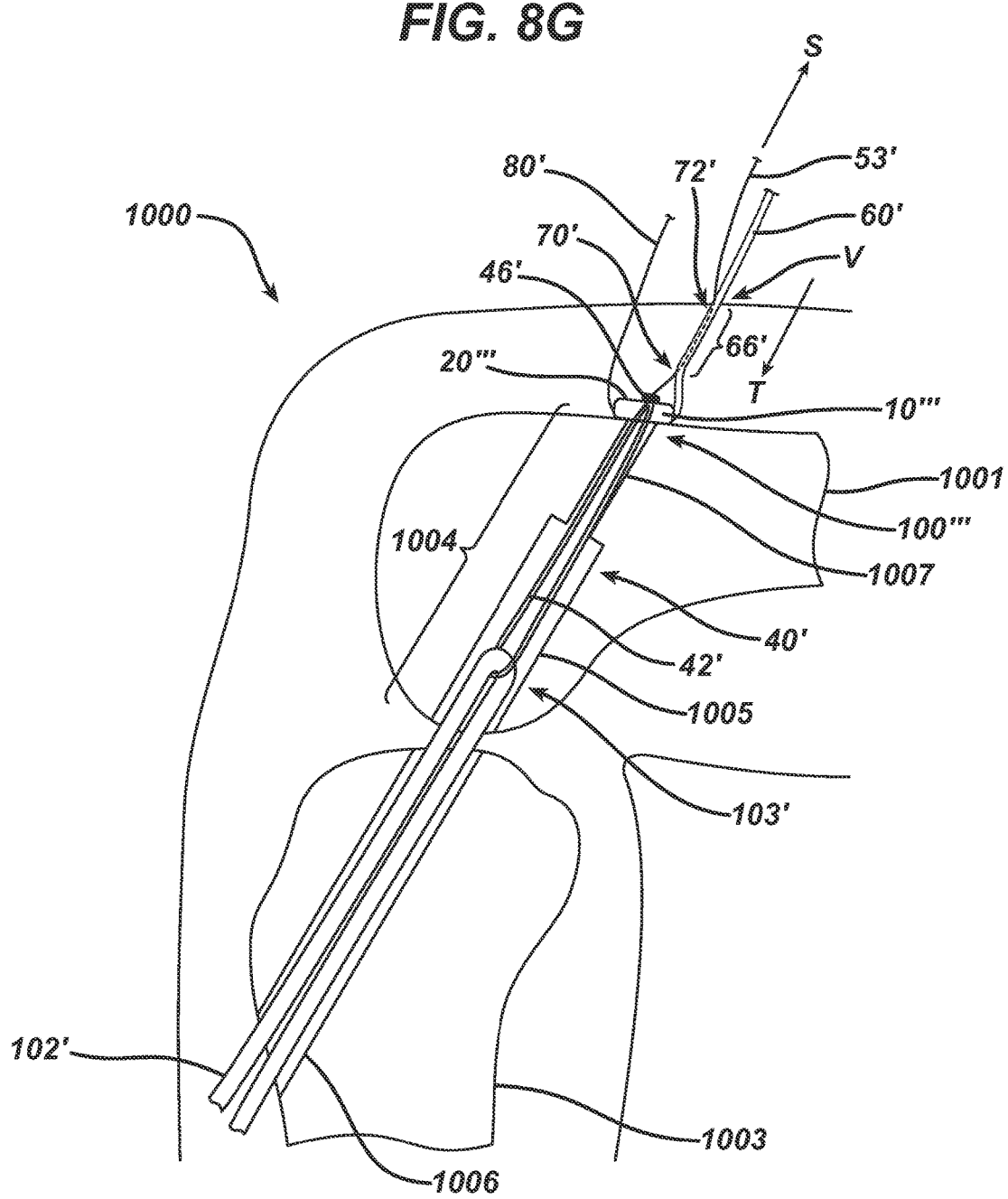
Figure 8H:
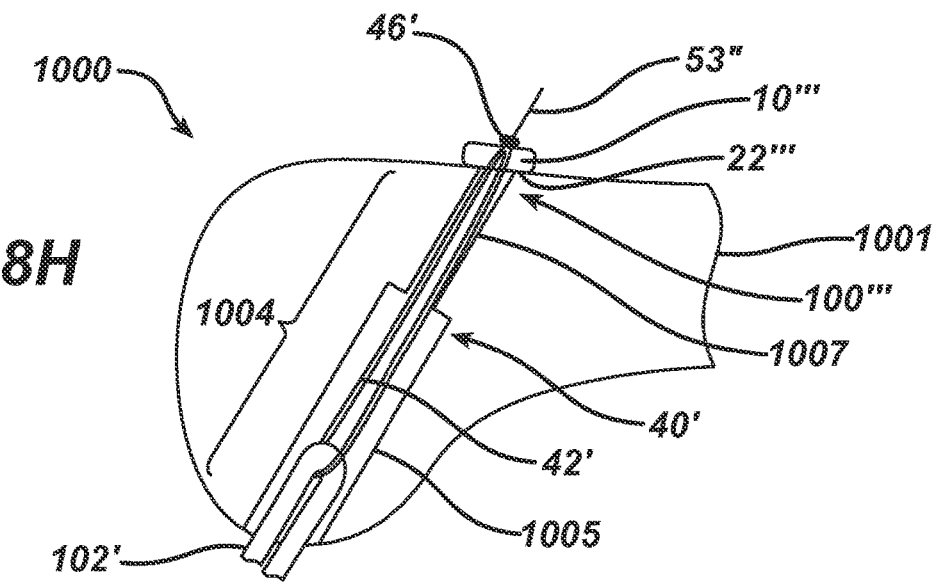

As shown in FIG. 8G, a force in an approximate direction S can be applied to the adjustable limb 53' to create tension therein. A force in an approximate opposite direction T can be applied to the leading filament 60', thereby causing the leading filament 60' to bunch at a location V that is proximate to the top surface 20''' of the body 10'''. The leading filament 60' and adjustable limb 53' can then be cut at a location near a second opening 72' of the leading filament 60' and the cut portions of filament can be removed. Further, if a trailing filament 80' is used, it too can be removed, for instance by pulling a terminal end of the filament 80' to pass the remaining portion of the filament through and out of a thru-hole in the body 10'''. Still further, the receiving portion 66' of the leading filament 60' that remains after the filament 60' is cut can also be removed as it is freely movable over the remaining portions of the adjustable limb 53'. Accordingly, as shown in FIGS. 8G and 8H, the portion of the limb 53' disposed between the knot 46' and the second opening 72' of the shuttle suture 60' is the only portion of the adjustable limb 53' that remains. The remaining portion of the adjustable limb 53' can help maintain the integrity of the knot 46' that defines the loop 42' at least by not being cut too short and being at risk for slipping or otherwise having the knot 46' unravel.

In other embodiments, a surgeon can select a different location to cut the leading filament 60' and the adjustable limb 53'. For example, a force in an approximate opposite direction T may not be supplied and the surgeon may cut the shuttle suture at a location that is between the first opening 70' and the second opening 72' of the leading filament 60', or at a location that is proximate to the first opening 70'. A person skilled in the art, in view of the present disclosure, will recognize a variety of other locations at which the leading filament 60' and associated adjustable limb 53' can be cut to still leave behind a desired length of the adjustable limb 53' without departing from the spirit of the present disclosure. Likewise, a person skilled in the art, in view of the present disclosure, will recognize a variety of other techniques that can be used to arrive at a desired location at which the leading filament 60' and associated adjustable limb 53' can be cut to still allow for a desired length of the adjustable limb 53' to remain after the cutting is performed without departing from the spirit of the present disclosure.

Figure 8I:
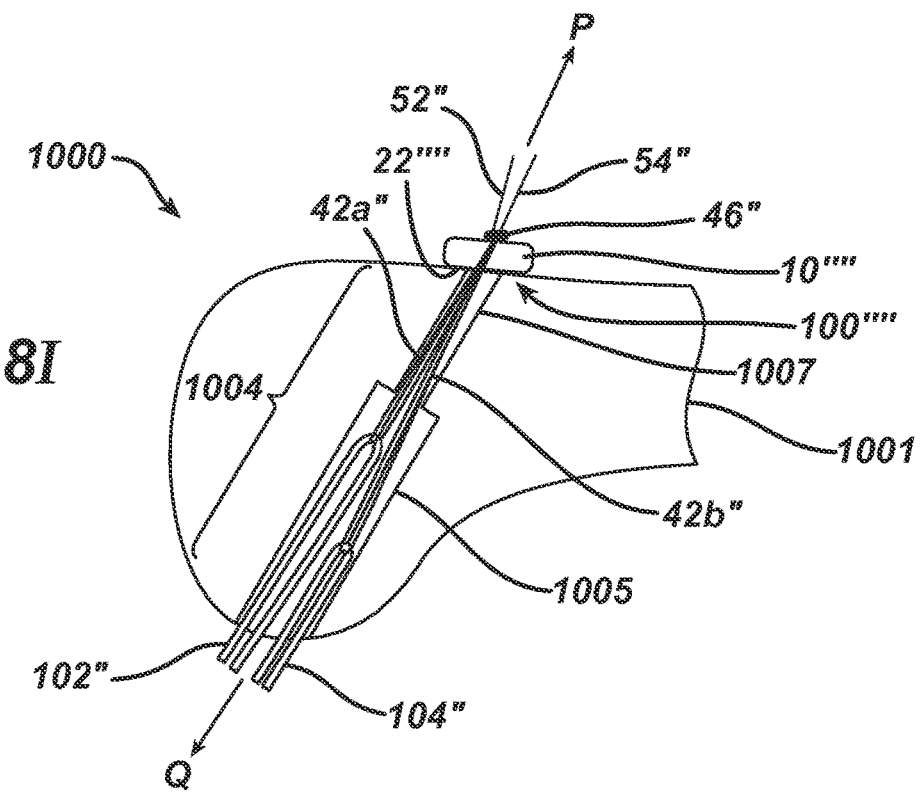
FIG. 8I is a schematic view of a portion of another exemplary embodiment for implanting a graft in a bone tunnel using a schematic surgical implant intended to represent the implant of FIG. 6 and having two grafts associated therewith.

FIG. 8I provides a second schematic representation of an implant 100'''' for use in ACL repairs, and is provided to illustrate the movement of two grafts 102'', 104'' within a bone tunnel, as shown the femoral tunnel 1004. A first loop 42a'' is formed from a first adjustable filament tail 52'' and is representative of the first and second coils 42a, 42c of the filament limb 52. A second loop 42b'' is formed from a second adjustable filament tail 54'' and is representative of the first and second coils 42b, 42c of the second limb 54. The first loop 42a'' is associated with the first graft 102'', and the second loop 42b'' is associated with the second graft 104'' using techniques described herein or otherwise known to those skilled in the art. As shown, the body or cortical button 10'''' is already oriented or flipped so that the bottom surface 22'' rests on the femoral cortex and faces the femoral tunnel 1004, for instance relying on techniques disclosed herein, and thus circumferences of the loops 42a'', 42b'' can be adjusted to selectively locate them within the femoral tunnel 1004. These techniques include, for instance, those discussed above with respect to FIGS. 5A and 5B.

In one exemplary embodiment, tension can be alternately applied in an approximate direction P to the adjustable filament tails 52'', 54'' to advance the grafts 102'', 104'' in increments of approximately 1 centimeter. Alternatively, the grafts 102'', 104'' can be advanced by using a configuration in which the adjustable filament tails 52'', 54'' are tied together and held in one hand while tension in the approximate direction Q is applied to the grafts 102'', 104'' by another hand. The surgeon can then alternate between pronation and supination to tighten the adjustable filament tails 52'', 54'', and thereby the coils of the loops 42a'', 42b'', which in turn advance the grafts 102'', 104'' proximally through the femoral tunnel 1004.

The grafts 102'', 104'' can be advanced to a desired location, for example up to the passing channel 1007 of the femoral tunnel 1004. When a graft reaches the passing channel 1007, typically the resistance to tightening of the coils of the loops noticeably increases. In some embodiments, such as that illustrated in FIG. 8I, a circumference of the first loop 42a'' can be smaller than a circumference of the second loop 42b'' so that one graft is more proximally located than the other graft.

The ability to control two independently tensioned ligament grafts in a single tunnel using a single cortical button is an improvement over existing techniques for ACL repairs. In existing methods for performing ACL repairs, a cortical button having filament associated therewith can only control a single bundle of ligament graft. Thus, if independent movement of multiple ligaments is needed, each ligament is typically associated with its own cortical button. Some surgeons use a double-tunnel technique to implant two ligaments, thus fixing each graft bundle in separate tunnels. Double-tunnel techniques likewise require one button per bundle. Thus, the methods described and resulting from disclosures herein represent improved ACL repair techniques because they allow for two ligament bundles to be independently moved using a single button, and doing so in a single tunnel. This results in procedures that have a reduced risk of complications and is generally less complex than existing procedures. Further, by disposing the adjustable limbs within a leading or shuttle filament used to manipulate the cortical button to a desired location, it can be easier to manage and control the filaments associated with the implant. Such a configuration also provides for an easy way to establish a desired length of the limb that is left behind so that the integrity of the knot of the loop is not compromised. A person skilled in the art will recognize that the disclosures pertaining to independently controlling two filament loops, and managing filaments by disposing them within a shuttle filament can be broadly applied to a variety of implant designs and surgical procedures, and can even be applied to non-medical fields without departing from the spirit of the present disclosure.

One skilled in the art will appreciate further features and advantages of the invention based on the above-described embodiments. Accordingly, the invention is not to be limited by what has been particularly shown and described, except as indicated by the appended claims. By way of non-limiting example, the exemplary ACL repair methods described herein with respect to FIGS. 8A-8I can be adapted for use with the other implant configurations described herein or derivable from the disclosures herein. All publications and references cited herein are expressly incorporated herein by reference in their entirety.

What is claimed is:

1. A surgical implant, comprising:
   an implantable body that includes a plurality of thru-holes formed therein;
   an adjustable filament loop coupled to the body, disposed through at least two of the thru-holes of the implantable body, the adjustable filament loop having at least one adjustable limb extending therefrom, the at least one adjustable limb being configured to adjust a size of the adjustable filament loop when tension is applied thereto; and
   a shuttle suture removably coupled to the implantable body, disposed through at least one of the thru-holes of the implantable body, the thru-hole through which the shuttle suture is disposed is a different thru-hole than any thru-hole through which the adjustable filament loop is disposed, the shuttle suture having at least a portion thereof that is hollow,
   wherein the at least one adjustable limb extends from the adjustable filament loop, into the hollow portion of the shuttle suture, and exits the shuttle suture at a location that is more remote from the implantable body than a location at which the adjustable limb entered the shuttle suture, and
   wherein the shuttle suture is disposed separate from the adjustable filament loop such that the shuttle suture does not form a portion of the adjustable filament loop.

2. The surgical implant of claim 1, wherein the adjustable filament loop comprises a plurality of coils formed as a result of suture of the adjustable filament loop being disposed through at least two of the plurality of thru-holes of the body such that a portion of each coil is disposed on the top side of the body and a portion of each coil is disposed on a bottom side of the body.

3. The surgical implant of claim 1, wherein the adjustable filament loop comprises a self-locking knot formed on a top side of the body.

4. The surgical implant of claim 1, wherein the at least one adjustable limb comprises a first adjustable limb and a second adjustable limb, the first limb extending into a first hollow portion of the shuttle suture and the second limb extending into a second hollow portion of the shuttle suture.

5. The surgical implant of claim 1, wherein the shuttle suture is disposed through a thru-hole formed in the implantable body and is configured to guide the implantable body, and the adjustable filament loop coupled thereto, through a passageway.

6. The surgical implant of claim 1, wherein the at least one adjustable limb enters the hollow portion of the shuttle suture at a location such that it is configured to form an acute angle with a longitudinal axis extending through a length of the implantable body.

7. The implant of claim 1, wherein the shuttle suture is configured to bunch in the hollow portion of the shuttle suture when tension is applied to the at least one adjustable limb in a first direction, away from the implantable body, and a force is applied to the shuttle suture in a second, substantially opposite direction, toward the implantable body.

8. A surgical implant, comprising:
an implantable body that includes a plurality of thru-holes formed therein;
an adjustable filament loop disposed through at least two of the plurality of thru-holes of the implantable body, the adjustable filament loop having at least one adjustable limb extending therefrom, the at least one adjustable limb being configured to adjust a size of the adjustable filament loop when tension is applied thereto; and
a shuttle suture removably coupled to the implantable body, the shuttle suture being disposed through at least one of the thru-holes of the implantable body, and the shuttle suture having at least a portion thereof that is hollow,
wherein the at least one adjustable limb extends from the adjustable filament loop, into the hollow portion of the shuttle suture, and exits the shuttle suture at a location that is more remote from the implantable body than a location at which the adjustable limb entered the shuttle suture,
wherein the shuttle suture is disposed separate from the adjustable filament loop such that the shuttle suture does not form a portion of the adjustable filament loop, and
wherein the at least one adjustable limb enters the hollow portion of the shuttle suture by passing through an opening disposed in a sidewall of the shuttle suture, the opening being disposed between the terminal ends of the shuttle suture such that the opening is not located at a terminal end of the shuttle suture.

9. The surgical implant of claim 8, wherein the at least one adjustable limb exits a second opening disposed in a sidewall of the shuttle suture, the second opening being disposed between the opening and one of the terminal ends of the terminal ends of the shuttle suture such that the second opening is not located at a terminal end of the shuttle suture.

10. The surgical implant of claim 8, wherein the thru-hole which the shuttle suture is disposed is a different thru-hole than any thru-hole through which the adjustable filament loop is disposed.

11. The surgical implant of claim 8, wherein the adjustable filament loop comprises a plurality of coils formed as a result of suture of the adjustable filament loop being disposed through at least two of the plurality of thru-holes of the body such that a portion of each coil is disposed on the top side of the body and a portion of each coil is disposed on a bottom side of the body.

12. The surgical implant of claim 8, wherein the adjustable filament loop comprises a self-locking knot formed on a top side of the body.

13. The surgical implant of claim 8, wherein the at least one adjustable limb comprises a first adjustable limb and a second adjustable limb, the first limb extending into a first hollow portion of the shuttle suture and the second limb extending into a second hollow portion of the shuttle suture.

14. The implant of claim 8, wherein the shuttle suture is configured to bunch in the hollow portion of the shuttle suture when tension is applied to the at least one adjustable limb in a first direction, away from the implantable body, and a force is applied to the shuttle suture in a second, substantially opposite direction, toward the implantable body.

15. A surgical implant, comprising:
a body having a plurality of thru-holes formed therein;
a first suture filament extending through the body and including:
a self-locking knot that defines a collapsible opening, and
one or more coils arranged such that each coil is formed as a result of the first suture filament being disposed through at least two of the plurality of thru-holes of the body such that a portion of each coil is disposed on the top side of the body and a portion of each coil is disposed on a bottom side of the body,
wherein first and second terminal ends of the first suture filament extend from the self-locking knot and are configured to adjust a size of one or more of the coils when tension is applied thereto; and
a second suture filament removably disposed through a thru-hole of the plurality of thru-holes, the thru-hole through which the second suture filament is disposed is a different thru-hole than any thru-hole through which the one or more coils is disposed, the second filament having at least a portion of a first limb that is hollow and at least a portion of a second limb that is hollow,
wherein the first terminal end of the first suture filament is disposed in at least a portion of the hollow portion of the first limb, and the second terminal end of the first suture filament is disposed in at least a portion of the hollow portion of the second limb, and
wherein the second suture filament is disposed separate from the one or more coils such that the second suture filament does not form a portion of the one or more coils.

16. The surgical implant of claim 15, wherein the first terminal end of the first suture filament exits a second opening disposed in a sidewall of the second suture filament, the second opening being disposed between the opening and one terminal end of terminal ends of the second suture filament such that the second opening is not located at a terminal end of the second suture filament.

17. The surgical implant of claim 15, wherein each of the first and second terminal ends exit the second suture filament at a location that is more remote from the body than a location at which the first and second terminal ends entered the second suture filament when tension is applied to the second suture filament.

18. The surgical implant of claim 15, wherein the thru-hole through which the second suture filament is disposed is a different thru-hole than the at least two thru-holes through which the first suture filament is disposed.

19. A surgical implant, comprising:
a body having a plurality of thru-holes formed therein;
a first suture filament extending through the body and including:
a self-locking knot that defines a collapsible opening, and one or more coils arranged such that each coil is formed as a result of the first suture filament being disposed through at least two of the plurality of thru-holes of the body such that a portion of each coil is disposed on the top side of the body and a portion of each coil is disposed on a bottom side of the body, wherein first and second terminal ends of the first suture filament extend from the self-locking knot and are configured to adjust a size of one or more of the one or more coils when tension is applied thereto; and a second suture filament removably disposed through a thru-hole of the plurality of thru-holes, the second filament having at least a portion of a first limb that is hollow and at least a portion of a second limb that is hollow, wherein the first terminal end of the first suture filament is disposed in at least a portion of the hollow portion of the first limb, and the second terminal end of the first suture filament is disposed in at least a portion of the hollow portion of the second limb, wherein the second suture filament is disposed separate from the one or more coils such that the second suture filament does not form a portion of the one or more coils, and wherein the first terminal end of the first suture filament enters the portion of the first limb of the second suture filament that is hollow by passing through an opening disposed in a sidewall of the second suture filament, the opening being disposed between terminal ends of the second suture filament such that the opening is not located at a terminal end of the second suture filament.

20. The surgical implant of claim 19, wherein the first terminal end of the first suture filament exits a second opening disposed in a sidewall of the second suture filament, the second opening being disposed between the opening and one terminal end of terminal ends of the second suture filament such that the second opening is not located at a terminal end of the second suture filament.

21. The surgical implant of claim 19, wherein each of the first and second terminal ends exit the second suture filament at a location that is more remote from the body than a location at which the first and second terminal ends entered the second suture filament when tension is applied to the second suture filament.

22. The surgical implant of claim 19, wherein the thru-hole through which the second suture filament is disposed is a different thru-hole than the at least two thru-holes through which the first suture filament is disposed.

* * * * *